US008506966B2

(12) United States Patent
Podda et al.

(10) Patent No.: US 8,506,966 B2
(45) Date of Patent: Aug. 13, 2013

(54) ADJUVANTED INFLUENZA VACCINES FOR PEDIATRIC USE

(75) Inventors: Audino Podda, Sovicille (IT); Nicola Groth, Buonconvento (IT); Michele Pellegrini, Castelnuovo Berardenga (IT)

(73) Assignee: Novartis AG, Basel (CH)

( * ) Notice: Subject to any disclaimer, the term of this patent is extended or adjusted under 35 U.S.C. 154(b) by 526 days.

(21) Appl. No.: 12/378,929

(22) Filed: Feb. 20, 2009

(65) Prior Publication Data
US 2009/0220546 A1 Sep. 3, 2009

Related U.S. Application Data

(60) Provisional application No. 61/066,791, filed on Feb. 22, 2008.

(51) Int. Cl.
*A61K 39/145* (2006.01)
*A61K 45/00* (2006.01)

(52) U.S. Cl.
USPC .................. 424/209.1; 424/210.1; 424/278.1; 424/283.1

(58) Field of Classification Search
None
See application file for complete search history.

(56) References Cited

U.S. PATENT DOCUMENTS

| 5,776,468 | A * | 7/1998 | Hauser et al. ............. 424/226.1 |
| 2004/0071734 | A1 | 4/2004 | Garcon et al. |
| 2004/0096463 | A1 | 5/2004 | Garcon et al. |
| 2004/0241187 | A1 | 12/2004 | Eichhorn |
| 2005/0220854 | A1 | 10/2005 | Maa et al. |

FOREIGN PATENT DOCUMENTS

| WO | WO-90/14837 A1 | 12/1990 |
| WO | WO-97/37000 A1 | 10/1997 |
| WO | WO-02/074336 A2 | 9/2002 |
| WO | WO-02/085446 A2 | 10/2002 |
| WO | WO-03/002069 A2 | 1/2003 |
| WO | WO-03/076601 A1 | 9/2003 |

OTHER PUBLICATIONS

Petrovsky et al. From Biopharminternational.com dated Aug. 2, 2007 downloaded Dec. 18, 2011.*
Higgins et al. Vaccine 1996 vol. 14, pp. 478-484.*
Podda et al. Expert Rev Vaccines 2003 vol. 2, pp. 197-204.*
Petrovsky et al. From Biopharminternational.com dated Aug. 2, 2007 downloaded Dec. 21, 2011.*
Aymard et al. (1980). "Rapid serodiagnosis of influenza by a modified radial haemolysis test: immune response," *Path. Biol.* 28(8):535-539.
Belshe et al. (Dec. 2001). "Safety, efficacy and effectiveness of cold-adapted, live, attenuated trivalent, intranasal influenza vaccine in adults and children," *Philosophical Transactions Roy. Soc. London Series B* 356:1947-1951.
Centers for Disease Control and Prevention. (Jul. 13, 2007). *MMWR* 56:1-53.
Chen et al. (Jul. 2004). "Epidermal powder immunization: cellular and molecular mechanisms for enhancing vaccine immunogenicity," *Virus Research* 103(1-2):147-153.
Chen et al. (Sep. 2001). "Serum and Mucosal Immune Responses to an Inactivated Influenza Virus Vaccine Induced by Epidermal Powder Immunization," *Immunization* 75(17):7956-7965.
Commitiee for Proprietary Medicinal Products (Mar. 1997). "Note for guidance on harmonisation of requirements for influenza vaccines," PMP/BWP/214/96 1-18.
Demicheli et al. (2006). "The Cochrane collaboration: Vaccines for preventing influenza in healthy children (Review)," *The Cochrane library*, Issue 3.
ECDC. "Technical report on the scientific panel on Vaccines and immunization: Infant and children seasonal immunization against influenza on a routine basis during inter-pandemic period." Stockholm, Jan. 2007.
Extended European Search Report dated Oct. 1, 2007, for EP application No. 05823432.9, filed Nov. 3, 2005, 5 pages.
Ferguson et al. (2003). *Nature* 422(6930):428-33.
Ghendon et al. (2006) *Epidemiol Infect* 134:71-78.
Halperin et al. (Dec. 1979). *AJPH* 69(12):1247-1251.
Hehme et al. (2002). "Ten years of experience with the trivalent split-influenza vaccine, Fluarix TM," *Clin. Drug Invest.* 22(11):751-769.
Heikkinen et al. (2004) *J Infect Dis* 190:1369-73.
Higgins et al. (1996). *Vaccine* 14(6):478-484.
International Search Report issued Jun. 26, 2006 for PCT/US05/39982, 3 pages.
Iskander et al. (2007) *Curr Opin Infect Dis* 20:259-263.
Izurieta et al. (2000) *NEJM* 342:232-39.
Kumagai et al. (Sep. 2004). *Vaccine* 22(25-26):3404-3410.
Knipe & Howley (2004). "Orthomyxoviridae: The Viruses and Their Replication" in *Fields Virology*, 4th Edition, Ch. 46, pp. 1487-1531.
Koelle et al. (2006). *Science* 314(5807):1898-903.
Lazar et al. (1980) *Infection and Immunity* 27(3):862-866.
Louie et al. (2006). *Pediatrics* 117(4): e610-8.
Maa et al. (Jul. 2004). "Influenza vaccine powder formulation development: Spray-Freeze-Drying and Stability evaluation," *J. Pharm. Sci.* 93(7):1912-1923.
Mitchell et al. (2005) *Pediatr Infect Dis J* 10:925-27.
Neuzil et al. (2000) *NEJM* 342:225-31.
O'Hagan, ed. (2000). *Vaccine Adjuvants: Preparation Methods and Research Protocols*, vol. 42 of Methods in Molecular Medicine series. ISBN: 1-59259-083-7.

(Continued)

*Primary Examiner* — Mary E Mosher
*Assistant Examiner* — Myron Hill
(74) *Attorney, Agent, or Firm* — Helen Lee; Otis Littlefield

(57) ABSTRACT

An influenza vaccine adjuvanted with a sub-micron oil-in-water emulsion elicits significantly higher immune responses in human pediatric populations. Compared to an existing unadjuvanted pediatric influenza vaccine, the adjuvanted vaccines provided herein can induce in children a longer persistence of high serum antibody titers and also longer seroconversion and seroprotection. The improvement in immune responses is seen for both influenza A virus and influenza B virus strains, but it is particularly marked for influenza B virus. Moreover, while the existing vaccine provides poor immunity in children after a single dose, the adjuvanted vaccine provides high seroprotection rates against the influenza A virus H3N2 subtype even after a single dose. Furthermore, the adjuvanted vaccine offers significantly better seroprotection against mismatched strains of influenza A virus.

7 Claims, 2 Drawing Sheets

(56) References Cited

OTHER PUBLICATIONS

Palmer et al. (1975). "Advanced laboratory technicals for immunological diagnostics," *Immunology ser. Nr.* 6, Procedural guide, 25-62.
Park et al. (Sep. 1-5, 2004). "Biodegradable polymer microneedles: fabrication, mechanics and transdermal drug delivery," *Proceedings of the 26th Annual International Conference of the IEEE EMBS*, San Francisco, CA, pp. 2654-2657.
Peltola et al. (2003) *Clin Infect Dis* 36:299-305.
Piascik (2003). "Intranasal Flu Vaccine Available This Season," *J. Am. Pharm. Assoc.* 43:728-730.
Plotkin & Orenstein, eds., (2004). *Vaccines*. 4th edition, ISBN: 0-7216-9688-0.
Podda & Del Giudice (2003) *Expert Rev Vaccines* 2:197-203.
Podda (2001) *Vaccine* 19:2673-80.
Poehling et al. (2006) *NEJM* 355:31-40.
Powell & Newman, eds., (1995). *Vaccine Design: The Subunit and Adjuvant Approach* Plenum Press (ISBN 0-306-44867-X).
Principi et al. (2003) *Pediatr Infect Dis J* 22(10 Suppl):S207-10.
Schild et al. (1975). "Single radial haemolysis: a new method for the assay of antibody to influenza haemagglutinin," *Bull. World Health Org.* 52:43-50.
Skowronski et al. (2007). *Vaccine* 25(15):2842-51.
Treanor et al. (1996) *J Infect Dis* 173:1467-70.
Walter et al. (2006) *Pediatrics* 118(3):e570-78.
Wollenberg et al. (2002) *J. Inverst. Dermatol.* 119:1096-1102.
Mikszta et al. (Apr. 2002). "Improved genetic immunization via micromechanical disruption of skin-barrier function and targeted epidermal delivery," Nature Medicine 8, 415-419.
Novartis International AG, (Oct. 22, 2010). "Novartis Phase III study indicates MF59® adjuvanted influenza vaccine, Fluad®, is 75 percent more efficacious than studied non-adjuvanted vaccines in young children," Novartis Media Release, 4 pages.
Carmona et al. (2010) "Immunogenicity and safety of AS03-adjuvanted 2009 influenza A H1N1 vaccine in children 6-35 months," Vaccine 28:5837-5844.
Esposito et al. (2011) "Influenza A/H1N1 MF59-adjuvanted vaccine in preterm and term children aged 6 to 23 months," Pediatrics 127(5):e1161-e1168.
Garcia-Sicilia et al. (2011) "Immunogenicity and safety of AS03-adjuvanted H1N1 pandemic vaccines in children and adolescents," Vaccine 29:4353-4361.
Garcon et al. (2012). "Development and evaluation of AS03, an adjuvant system containing α-tocopherol and squalene in an oil-in-water emulsion," Expert Rev. Vaccines 11(3):349-366.
Gilca et al. (2011) "Effectiveness of pandemic H1N1 vaccine against influenza-related hospitalization in children," Pediatrics 128:e1084-e1091.
Vesikari et al. (2009) "Enhanced immunogenicity of seasonal influenza vaccines in young children using MF59 adjuvant," Pediatric Infectious Disease Journal 28(7):563-571.
Vesikari et al. (2011) "Oil-in-water emulsion adjuvant with influenza vaccine in young children," New England Journal of Medicine 365(15):1406-1416.
Bruhl, P. et al, Humoral and cell-mediated immunity to vero cell-derived influenza vaccine, Vaccine, 2000, vol. 19, No. 9-10, p. 1149-58.
Cormier, M. et al, Macroflux technology for transdermal delivery of therapeutic proteins and vaccines, Drugs and the Pharmaceutical Sciences, 2003, vol. 126, p. 589-598.
Cormier, M. et al, Transdermal delivery of desmopressin using a coated microneedle array patch system, Journal of controlled release: official journal of the Controlled Release Society, Jul. 2004, vol. 97, No. 3, p. 503-11.
Macroflux transdermal technology development for the delivery of therapeutic peptides and proteins, Drug Delivery Technology, 2002, vol. 2, No. 5.
Matriano, J. A. et al, Macroflux microprojection array patch technology: a new and efficient approach for intracutaneous immunization, Pharm Res, 2002, vol. 19, No. 1, p. 63-70.
Pau, M. G. et al, The human cell line PER.C6 provides a new manufacturing system for the production of influenza vaccines, Vaccine, 2001, vol. 19, No. 17-19, p. 2716-21.

\* cited by examiner

ADJUVANTED INFLUENZA VACCINES FOR PEDIATRIC USE

This applications claims priority from provisional application 61/066,791 filed Feb. 22, 2008, the complete contents of which are incorporated in full herein by reference.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 223002117400SeqList.txt, date recorded: Aug. 22, 2011, size: 1 KB).

TECHNICAL FIELD

This invention is in the field of adjuvanted vaccines for protecting against influenza virus infection.

BACKGROUND ART

Influenza vaccines currently in general use are described in chapters 17 & 18 of reference 1. They are based on live virus or inactivated virus, and inactivated vaccines can be based on whole virus, 'split' virus or on purified surface antigens (including haemagglutinin and neuraminidase).

The burden of influenza in healthy young children has been increasingly recognized along with new studies on the medical [2-7] and the socioeconomic [8] impact of influenza. Moreover, children have the highest attack rates of influenza during epidemic periods, and transmit influenza viruses in the community to the high risk groups [8,9].

The American Advisory Committee on Immunization Practices (ACIP) in 2006 recommended annual influenza vaccination for all children aged 6-59 months, because children aged 6-23 months are at substantially increased risk for influenza-related hospitalizations [2-7] and children aged 24-59 months are at increased risk for influenza-related clinic and emergency department visits [6]. In July 2008 the ACIP further extended the recommendation for seasonal influenza vaccination in adolescents aged 5 to 18 years [10]. In Europe, some countries have issued similar recommendations, although the European CDC has taken a more restricted position with regard to universal immunization of young children, noting that efficacy in children under 24 months of age has been insufficiently documented and might be as low as 37% [11]. A Cochrane analysis stated that "the field efficacy of influenza vaccine in young children is not different from placebo" [12].

In addition to modest efficacy, conventional vaccines do not appear to induce satisfactory protective antibodies in unprimed children, especially the very young ones. More specifically, conventional vaccines generally show lower immunogenicity against the influenza B strain than against influenza A strains [13, 14]. ACIP has since 2004 recommended a two-dose vaccination regimen in immunologically naïve very young children, but more recently such recommendation has been extended to children aged up to 8 years of age, because of the accumulating evidence indicating that 2 doses are required for protection in this population [15].

An additional problem in immunizing children against influenza comes from 'antigenic drift'. Influenza viruses routinely undergo intense selection to evade the host immune system, resulting in genetic variation and the generation of novel strains ('antigenic drift'). It has been suggested that antigenic drift is associated with a more severe and early onset of influenza epidemic, since the level of pre-existing immunity to the drifted strain is reduced to the drifted strain [16]. While all three virus strains currently included in seasonal influenza vaccines are subject to antigenic drift, the A/H3N2 strain is known to drift more frequently and new variants tend to replace old ones [17, 18].

The pace of antigenic drift can exceed the pace of vaccine manufacture. When a vaccine is released, therefore, the vaccine strains may no longer be a good match for the circulating strains. A vaccine mismatch can result in a significant excess of influenza-related mortality, since vaccine effectiveness is reduced [19]. Vaccine mismatch is a potentially larger problem in the most influenza susceptible populations, particularly in young children who do not have pre-existing immunity against any influenza viruses. This was shown more recently in the 2003/2004 season by the emergence of a drifted mismatch strain (A/Fujian, H3N2), which was not included in the vaccine, and resulted in 3 times as many children being hospitalized in intensive care in California, compared with the previous season [20]. In contrast to young children, the elderly at least have a significant history of prior exposure to circulating influenza strains, which offers them some degree of cross protection. Drifted influenza strains which emerge after vaccine recommendations are finalized, as occurred in 1997 and 2003, are a significant threat to vaccine-naYve young children.

It is an object of the invention to provide influenza vaccines that are effective in children, that adequate influenza B virus immunogenicity (to induce an adequate immune response), that give useful protection against common circulating influenza viruses even after a single dose, and/or that are effective in children against drifted influenza A virus strains, particularly A/H3N2 strains.

SUMMARY OF THE INVENTION

It has now been found that an influenza vaccine adjuvanted with a sub-micron oil-in-water emulsion elicits significantly improved immune responses in human pediatric populations. Compared to an existing unadjuvanted pediatric influenza vaccine the adjuvanted vaccines provided herein can induce in children a longer persistence of high serum antibody titers and also longer seroconversion and seroprotection. The improvement in immune responses is seen for both influenza A virus and influenza B virus strains, but it is particularly marked for influenza B virus. Moreover, while the existing vaccine provides poor immunity in children after a single dose, the adjuvanted vaccine provides high seroprotection rates against the influenza A virus H3N2 subtype even after a single dose. Furthermore, the adjuvanted vaccine offers significantly better seroprotection against mismatched strains of influenza A virus.

Thus the invention provides an influenza vaccine for use in a child, comprising: (i) an influenza virus antigen; and (ii) an adjuvant.

The invention also provides an immunogenic composition for use in immunizing a child, wherein the composition comprises: (i) an influenza virus antigen; and (ii) an adjuvant.

The invention also provides an immunogenic composition for immunizing a child, wherein the composition comprises: (i) an influenza virus antigen; and (ii) an adjuvant.

The invention also provides (i) an influenza virus antigen and (ii) an adjuvant, in the manufacture of an immunogenic composition for immunizing a child.

The invention also provides a method for raising an immune response in a child, comprising a step of administering to the child an immunogenic composition comprising: (i) an influenza virus antigen; and (ii) an adjuvant. Preferably this step is performed on a particular child only once per influenza season.

The invention also provides a composition in unit dosage form, wherein: the composition comprises (i) an influenza virus antigen and (ii) an adjuvant; and the unit dosage has a volume less than 0.5 ml e.g. a volume of between 0.2 ml and 0.3 ml, for example about 0.25 ml.

The invention also provides a composition in unit dosage form, wherein: the composition comprises (i) an influenza virus antigen and (ii) an adjuvant; and the unit dosage contains between 6 and 9 µg of influenza hemagglutinin per influenza virus strain e.g. between 7-8 µg/strain, or about 7.5 µg/strain.

The child being immunized may be aged between 0 months and 36 months e.g. between 6 months and 35 months, between 6 months and 30 months, between 6 months and 24 months, between 6 months and 23 months (all inclusive). Immunization is ideal after a child is 6 months old but before their third birthday, as described in more detail below. The invention can also be used with older children e.g. up to 72 months of age. Thus the child may be between 6 and 72 months old, etc. and so a vaccine may be administered before a child's sixth birthday.

The invention is particularly useful for raising a useful immune response against subtype H3N2 of influenza A virus after a single dose, and against both subtype H1N1 of influenza A virus and influenza B virus after two doses. It may also be used to provide immunity against pandemic strains. The invention is particularly useful in protecting against drifted strains of influenza A virus.

An adjuvanted vaccine that can be used according to the invention is the FLUAD™ product, which is already available but is approved for use only in elderly subjects i.e. subjects at least 65 years of age (or, in some regions, at least 60 years of age). The adjuvant in this vaccine is a sub-micron oil-in-water emulsion known as MF59. The adjuvant in FLUAD™ helps to overcome the age-related immuno-senescence seen in the elderly.

DETAILED DESCRIPTION

The Influenza Virus Antigen

Figure 1:
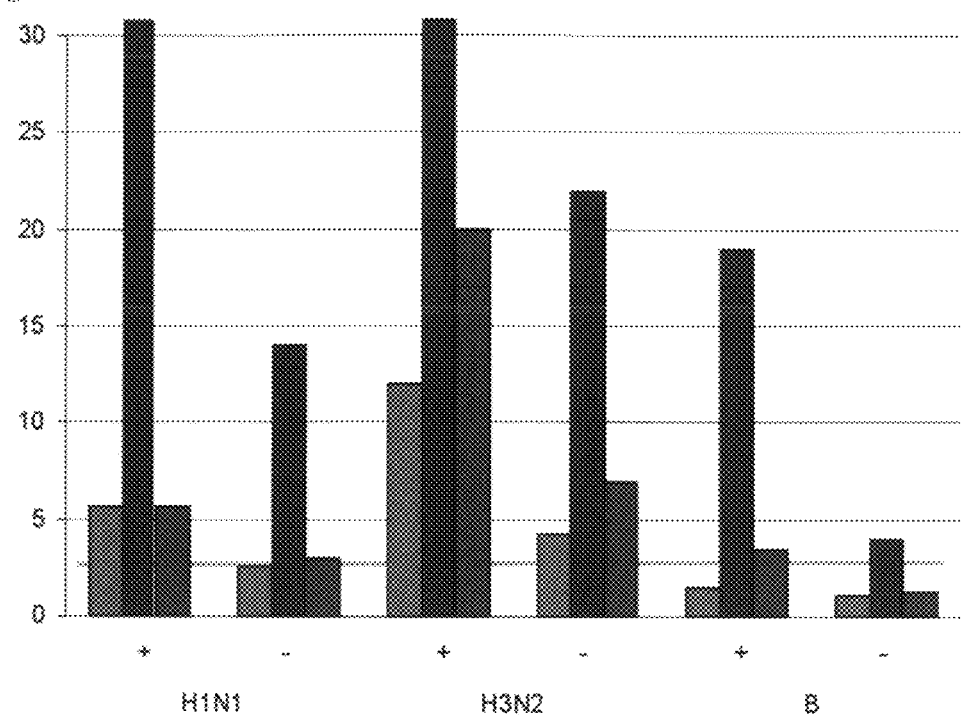
FIG. 1 shows GMRs. In each of the six groups of 3 bars the values are the ratios of GMTs at (i) day 29, (ii) day 50 and (iii) day 209, against the GMT at day 1. The six groups are in three pairs, each pair being with (+) or without (−) adjuvant. The three pairs are from left to right: H1N1, H3N2 and B. The horizontal bar shows the CPMP criterion for adult vaccines. Two of the +bars exceed the vertical axis: with H1N1 the GMR at day 50 was 33; with H3N2 it was 61.
Figure 2:
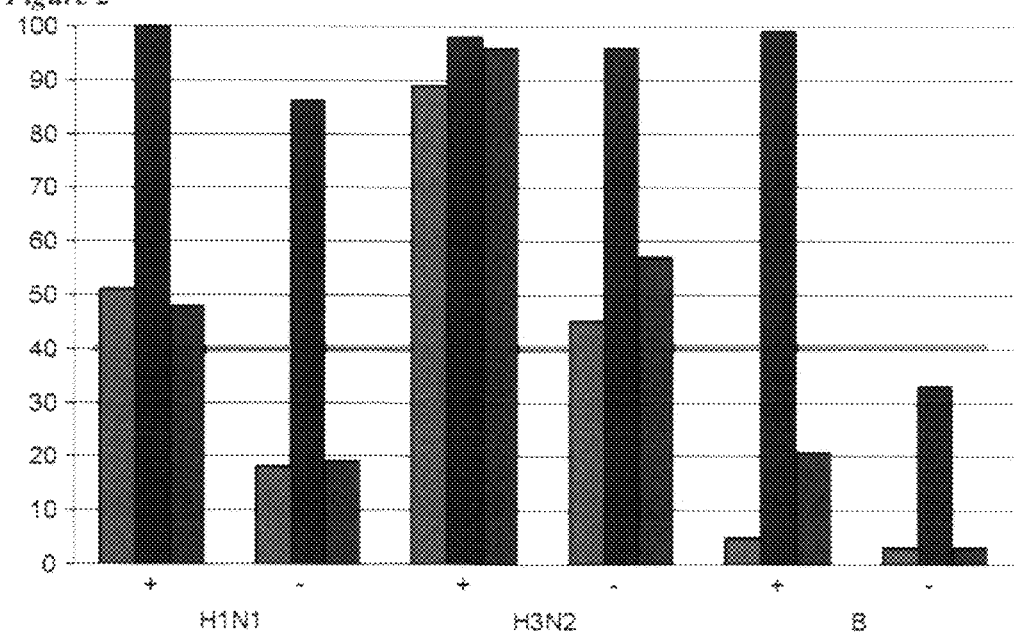
FIG. 2 shows SC or SI rates, arranged as in FIG. 1, but each group of three bars shows percentages at days 29, 50 and 209.
Figure 3:
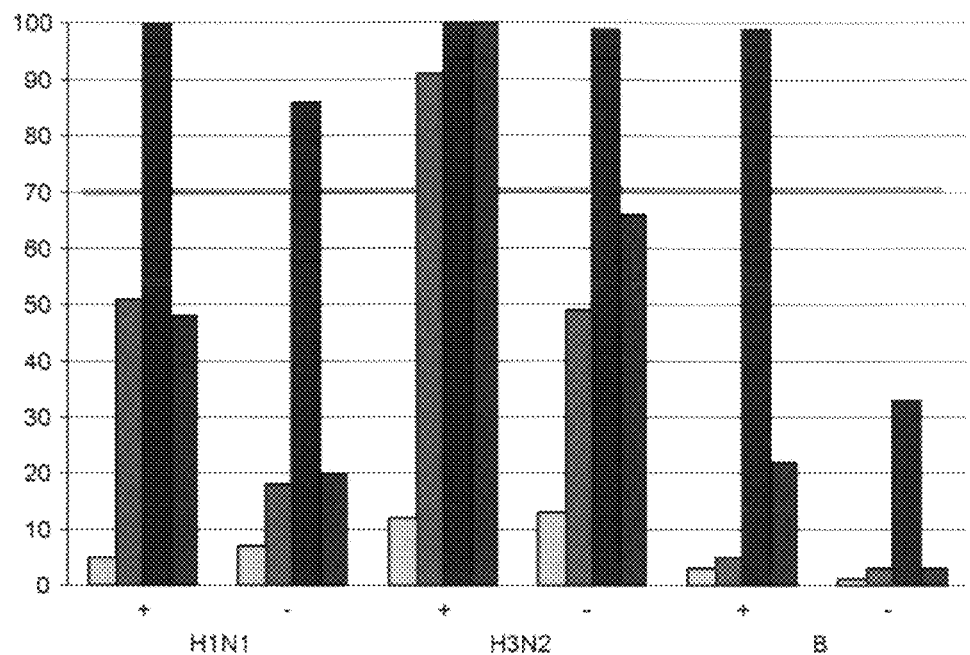
FIG. 3 shows seroprotection rates, arranged as in FIG. 1, but each group of four bars showing percentages at days 1, 29, 50 and 209.

The invention uses an influenza virus antigen to immunize a child. The antigen will typically be prepared from influenza virions but, as an alternative, antigens such as haemagglutinin can be expressed in a recombinant host (e.g. in an insect cell line using a baculovirus vector) and used in purified form [21,22]. In general, however, antigens will be from virions.

The antigen may take the form of a live virus or, more preferably, an inactivated virus. Chemical means for inactivating a virus include treatment with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. The INFLEXAL™ product is a whole virion inactivated vaccine.

Where an inactivated virus is used, the vaccine may comprise whole virion, split virion, or purified surface antigens (including hemagglutinin and, usually, also including neuraminidase).

An inactivated but non-whole cell vaccine (e.g. a split virus vaccine or a purified surface antigen vaccine) may include matrix protein, in order to benefit from the additional T cell epitopes that are located within this antigen. Thus a non-whole cell vaccine (particularly a split vaccine) that includes haemagglutinin and neuraminidase may additionally include M1 and/or M2 matrix protein. Useful matrix fragments are disclosed in reference [23]. Nucleoprotein may also be present.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents and/or solvents to produce subvirion preparations, including the 'Tween-ether' splitting process. Methods of splitting influenza viruses are well known in the art e.g. see refs. [24-29], etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants. Suitable splitting agents include, but are not limited to: ethyl ether, polysorbate 80, deoxycholate, tri-N-butyl phosphate, alkylglycosides, alkylthioglycosides, acyl sugars, sulphobetaines, betaines, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), nonoxynol 9 (NP9) Sympatens-NP/090,) polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Another form of inactivated influenza antigen is the virosome [30] (nucleic acid free viral-like liposomal particles). Virosomes can be prepared by solubilization of influenza virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane. The invention can be used to store bulk virosomes. as in the INFLEXAL V™ and INVAVAC™ products. In some embodiments, the influenza antigen is not in the form of a virosome.

The influenza virus may be attenuated. The influenza virus may be temperature-sensitive. The influenza virus may be cold-adapted. These three features are particularly useful when using live virus as a vaccine antigen.

HA is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [31,32]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 1.9, about 1.5, etc. per strain. A dose of 7.5 μg per strain is ideal for use in children.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza virus strains for use in vaccines change from season to season. In the current inter-pandemic period, vaccines typically include two influenza A strains (H1N1 and H3N2) and one influenza B strain, and trivalent vaccines are typical. The invention may also use viruses from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may protect against one or more of influenza A virus hemagglutinin subtypes H1, H2, H3, H4, H5, H6, H7, H8, H9, H10, H11, H12, H13, H14, H15 or H16. The virus may additionally have any of NA subtypes N1, N2, N3, N4, N5, N6, N7, N8 or N9.

The invention can be used with pandemic influenza A virus strains. Characteristics of a pandemic strain are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the vaccine recipient and the general human population are immunologically naïve to the strain's hemagglutinin; (b) it is capable of being transmitted horizontally in the human population; and (c) it is pathogenic to humans. Pandemic strains H2, H5, H7 or H9 subtype strains e.g. H5N1, H5N3, H9N2, H2N2, H7N1 and H7N7 strains. Within the H5 subtype, a virus may fall into a number of clades e.g. clade 1 or clade 2. Six sub-clades of clade 2 have been identified with sub-clades 1, 2 and 3 having a distinct geographic distribution and are particularly relevant due to their implication in human infections.

Influenza B virus currently does not display different HA subtypes, but influenza B virus strains do fall into two distinct lineages. These lineages emerged in the late 1980s and have HAs which can be antigenically and/or genetically distinguished from each other [33]. Current influenza B virus strains are either B/Victoria/2/87-like or B/Yamagata/16/88-like. These strains are usually distinguished antigenically, but differences in amino acid sequences have also been described for distinguishing the two lineages e.g. B/Yamagata/16/88-like strains often (but not always) have HA proteins with deletions at amino acid residue 164, numbered relative to the 'Lee40' HA sequence [34]. The invention can be used with antigens from a B virus of either lineage (or both).

Compositions may include antigen(s) from one or more (e.g. 1, 2, 3, 4 or more) influenza virus strains, including influenza A virus and/or influenza B virus. Trivalent vaccines are most typical for use with the invention, as described above, but in some embodiments a composition includes antigen from two influenza A virus strains and two influenza B virus strains (e.g. a tetravalent "ABBA" vaccine), for example with hemagglutinin from: (i) a A/H1N1 strain; (ii) a A/H3N2 strain; (iii) a B/Victoria/2/87-like strain; and (iv) B/Yamagata/16/88-like strain. Where a vaccine includes more than one strain of influenza, the different strains are typically grown separately and are mixed after the viruses have been harvested and antigens have been prepared. Thus a process of the invention may include the step of mixing antigens from more than one influenza strain.

An influenza virus used with the invention may be a reassortant strain, and may have been obtained by reverse genetics techniques. Reverse genetics techniques [e.g. 35-39] allow influenza viruses with desired genome segments to be prepared in vitro using plasmids. Typically, it involves expressing (a) DNA molecules that encode desired viral RNA molecules e.g. from polI promoters or bacteriophage RNA polymerase promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA can be used [40-42], and these methods will also involve the use of plasmids to express all or some (e.g. just the PB1, PB2, PA and NP proteins) of the viral proteins, with up to 12 plasmids being used in some methods. To reduce the number of plasmids needed, a recent approach [43] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference Error! Bookmark not defined. method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [44]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [45,46].

Thus an influenza A virus may include one or more RNA segments from a A/PR/8/34 virus (typically 6 segments from A/PR/8/34, with the HA and N segments being from a vaccine strain, i.e. a 6:2 reassortant). It may also include one or more RNA segments from a A/WSN/33 virus, or from any other virus strain useful for generating reassortant viruses for vaccine preparation. An influenza A virus may include fewer than 6 (i.e. 0, 1, 2, 3, 4 or 5) viral segments from an AA/6/60 influenza virus (A/Ann Arbor/6/60). An influenza B virus may include fewer than 6 (i.e. 0, 1, 2, 3, 4 or 5) viral segments from an AA/1/66 influenza virus (B/Ann Arbor/1/66). Typically, the invention protects against a strain that is capable of human-to-human transmission, and so the strain's genome will usually include at least one RNA segment that originated in a mammalian (e.g. in a human) influenza virus. It may include NS segment that originated in an avian influenza virus.

Strains whose antigens can be included in the compositions may be resistant to antiviral therapy (e.g. resistant to oseltamivir [47] and/or zanamivir), including resistant pandemic strains [48].

HA used with the invention may be a natural HA as found in a virus, or may have been modified. For instance, it is known to modify HA to remove determinants (e.g. hyper-basic regions around the cleavage site between HA1 and HA2) that cause a virus to be highly pathogenic in avian species, as these determinants can otherwise prevent a virus from being grown in eggs.

The viruses used as the source of the antigens can be grown either on eggs (e.g. specific pathogen free eggs) or on cell culture. The current standard method for influenza virus growth uses embryonated hen eggs, with virus being purified from the egg contents (allantoic fluid). More recently, however, viruses have been grown in animal cell culture and, for reasons of speed and patient allergies, this growth method is preferred.

The cell line will typically be of mammalian origin. Suitable mammalian cells of origin include, but are not limited to, hamster, cattle, primate (including humans and monkeys) and dog cells, although the use of primate cells is not preferred. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [49-51]. Suitable dog cells are e.g. kidney cells, as in the CLDK and MDCK cell lines.

Thus suitable cell lines include, but are not limited to: MDCK; CHO; CLDK; HKCC; 293T; BHK; Vero; MRC-5; PER.C6 [52]; FRhL2; WI-38; etc. Suitable cell lines are widely available e.g. from the American Type Cell Culture (ATCC) collection [53], from the Coriell Cell Repositories [54], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940.

The most preferred cell lines are those with mammalian-type glycosylation. As a less-preferred alternative to mammalian cell lines, virus can be grown on avian cell lines [e.g. refs. 55-57], including cell lines derived from ducks (e.g. duck retina) or hens. Examples of avian cell lines include avian embryonic stem cells [55,58] and duck retina cells [56]. Suitable avian embryonic stem cells, include the EBx cell line derived from chicken embryonic stem cells, EB45, EB14, and EB14-074 [59]. Chicken embryo fibroblasts (CEF) may also be used. Rather than using avian cells, however, the use of mammalian cells means that vaccines can be free from avian DNA and egg proteins (such as ovalbumin and ovomucoid), thereby reducing allergenicity.

The most preferred cell lines for growing influenza viruses are MDCK cell lines [60-63], derived from Madin Darby canine kidney. The original MDCK cell line is available from the ATCC as CCL-34, but derivatives of this cell line may also be used. For instance, reference 60 discloses a MDCK cell line that was adapted for growth in suspension culture ('MDCK 33016', deposited as DSM ACC 2219). Similarly, reference 64 discloses a MDCK-derived cell line that grows in suspension in serum-free culture ('B-702', deposited as FERM BP-7449). Reference 65 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 66 discloses MDCK cell lines with high susceptibility to infection, including 'MDCK.5F1' cells (ATCC CRL-12042). Any of these MDCK cell lines can be used.

Virus may be grown on cells in adherent culture or in suspension. Microcarrier cultures can also be used. In some embodiments, the cells may thus be adapted for growth in suspension.

Cell lines are preferably grown in serum-free culture media and/or protein free media. A medium is referred to as a serum-free medium in the context of the present invention in which there are no additives from serum of human or animal origin. The cells growing in such cultures naturally contain proteins themselves, but a protein-free medium is understood to mean one in which multiplication of the cells occurs with exclusion of proteins, growth factors, other protein additives and non-serum proteins, but can optionally include proteins such as trypsin or other proteases that may be necessary for viral growth.

Cell lines supporting influenza virus replication are preferably grown below 37° C. [67] (e.g. 30-36° C., or at about 30° C., 31° C., 32° C., 33° C., 34° C., 35° C., 36° C.) during viral replication.

Methods for propagating influenza virus in cultured cells generally includes the steps of inoculating a culture of cells with an inoculum of the strain to be grown, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture e.g. before inoculation, at the same time as inoculation, or after inoculation [67].

In preferred embodiments, particularly with MDCK cells, a cell line is not passaged from the master working cell bank beyond 40 population-doubling levels.

The viral inoculum and the viral culture are preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [68]. Absence of herpes simplex viruses is particularly preferred.

Where virus has been grown on a cell line then it is standard practice to minimize the amount of residual cell line DNA in the final vaccine, in order to minimize any oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 μg of haemagglutinin are more preferred, as are vaccines containing <10 ng (e.g. <1 ng, <100 pg) host cell DNA per 0.5 ml volume.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references [69] & [70], involving a two-step treatment, first using a DNase (e.g. Benzonase), which may be used during viral growth, and then a cationic detergent (e.g. CTAB), which may be used during virion disruption. Removal by β-propiolactone treatment can also be used.

Measurement of residual host cell DNA is now a routine regulatory requirement for biologicals and is within the normal capabilities of the skilled person. The assay used to measure DNA will typically be a validated assay [71,72]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three main techniques for DNA quantification can be used: hybridization methods, such as Southern blots or slot blots [73]; immunoassay methods, such as the Threshold™ System [74]; and quantitative PCR [75]. These methods are all familiar to the skilled person, although the precise characteristics of each method may depend on the host cell in question e.g. the choice of probes for hybridization, the choice of primers and/or probes for amplification, etc. The Threshold™ system from *Molecular Devices* is a quantitative assay for picogram levels of total DNA, and has been used for monitoring levels of contaminating DNA in biopharmaceuticals [74]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 76.

The Adjuvant

Compositions of the invention include an adjuvant, which can function to enhance the immune responses (humoral and/or cellular) elicited in a patient who receives the composition. Vaccine adjuvants that can be used with the invention include, but are not limited to:

A mineral-containing composition, including calcium salts and aluminum salts (or mixtures thereof). Calcium salts include calcium phosphate (e.g. the "CAP" particles disclosed in ref. 77). Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt [78]. The adjuvants known as aluminum hydroxide and aluminum phosphate may be used. These names are conventional, but are used for convenience only, as neither is a precise description of the actual chemical compound which is present (e.g. see chapter 9 of reference 162). The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. The invention can use a mixture of both an aluminium hydroxide and an aluminium phosphate. In this case there may be more aluminium phosphate than hydroxide e.g. a weight ratio of at least 2:1 e.g. $\geq$5:1, $\geq$6:1, $\geq$7:1, $\geq$8:1, $\geq$9:1, etc. The concentration of $Al^{+++}$ in a composition for administration to a patient is preferably less than 10 mg/ml e.g. ≦5 mg/ml, ≦4 mg/ml, ≦3 mg/ml, ≦2 mg/ml, ≦1 mg/ml, etc. A preferred range is between 0.3 and 1 mg/ml. A maximum of 0.85 mg/dose is preferred.

Saponins [chapter 22 of ref. 162], which are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™. Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 79. Saponin formulations may also comprise a sterol, such as cholesterol [80]. Combinations of saponins and cholesterols can be used to form unique particles called immunostimulating complexes (ISCOMs) [chapter 23 of ref. 162]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 80-82. Optionally, the ISCOMS may be devoid of additional detergent [83]. A review of the development of saponin based adjuvants can be found in refs. 74 & 85.

Bacterial ADP-ribosylating toxins (e.g. the *E. coli* heat labile enterotoxin "LT", cholera toxin "CT", or pertussis toxin "PT"), and in particular detoxified derivatives thereof, such as the mutant toxins known as LT-K63 and LT-R72 [86] or CT-E29H [87]. The use of detoxified ADP-ribosylating toxins as mucosal adjuvants is described in ref. 88 and as parenteral adjuvants in ref. 89.

Bioadhesives and mucoadhesives, such as esterified hyaluronic acid microspheres [90] or chitosan and its derivatives [91].

Microparticles (i.e. a particle of ~100 nm to ~150 μm in diameter, more preferably ~200 nm to ~30 μm in diameter, or ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB).

Liposomes (Chapters 13 & 14 of ref. 162). Examples of liposome formulations suitable for use as adjuvants are described in refs. 92-94.

Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").

A polyoxidonium polymer [95,96] or other N-oxidized polyethylene-piperazine derivative.

Methyl inosine 5'-monophosphate ("MIMP") [97].

A polyhydroxlated pyrrolizidine compound [98], such as one having formula:

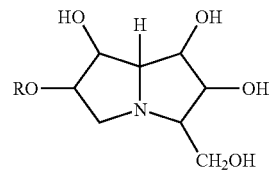

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [99-106] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma insulin [107] or derivative thereof, such as algammulin.

An oil-in-water emulsion. Various such emulsions are known, and they typically include at least one oil and at least one surfactant, with the oil(s) and surfactant(s) being biodegradable (metabolisable) and biocompatible. Further details are given below.

An immunostimulatory oligonucleotide, such as one containing a CpG motif (a dinucleotide sequence containing an unmethylated cytosine residue linked by a phosphate bond to a guanosine residue), or a CpI motif (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded. References 108, 109 and 110 disclose possible analog substitutions e.g. replacement of guanosine with 2'-deoxy-7-deazaguanosine. The adjuvant effect of CpG oligonucleotides is further discussed in refs. 111-116. A CpG sequence may be directed to TLR9, such as the motif GTCGTT or TTCGTT [117]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 118-120. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 117 and 121-123. A useful CpG adjuvant is CpG7909, also known as ProMune™ (Coley Pharmaceutical Group, Inc.). Another is CpG1826. As an alternative, or in addition, to using CpG sequences, TpG sequences can be used [124], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref. 124), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 124), and/or it may have a nucleotide composition with >25% cytosine (e.g. >35%, >40%, >50%, >60%, >80%, etc.). These oligonucleotides may be free from unmethylated CpG motifs. Immunostimulatory oligonucleotides will typically comprise at least 20 nucleotides. They may comprise fewer than 100 nucleotides.

A particularly useful adjuvant based around immunostimulatory oligonucleotides is known as IC31™ [125]. Thus an adjuvant used with the invention may comprise a mixture of (i) an oligonucleotide (e.g. between 15-40 nucleotides) including at least one (and preferably multiple) CpI motifs, and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{13}$-3' (SEQ ID NO: 1). The polycationic polymer may be a peptide comprising 11-mer amino acid sequence KLKLLLLLKLK (SEQ ID NO: 2).

3-O-deacylated monophosphoryl lipid A ('3dMPL', also known as 'MPL™') [126-129]. In aqueous conditions, 3dMPL can form micellar aggregates or particles with different sizes e.g. with a diameter <150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [130]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm.

An imidazoquinoline compound, such as Imiquimod ("R-837") [131,132], Resiquimod ("R-848") [133], and their analogs; and salts thereof (e.g. the hydrochloride salts). Further details about immunostimulatory imidazoquinolines can be found in references 134 to 138.

A thiosemicarbazone compound, such as those disclosed in reference 139. Methods of formulating, manufacturing, and screening for active compounds are also described in reference 139. The thiosemicarbazones are particularly effective in the stimulation of human peripheral blood mononuclear cells for the production of cytokines, such as TNF-α.

A tryptanthrin compound, such as those disclosed in reference 140. Methods of formulating, manufacturing, and screening for active compounds are also described in reference 140. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

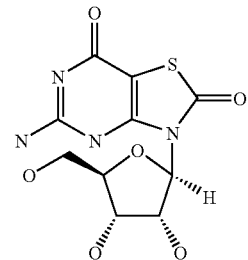 [SMILES: Nc1nc(=O)c2sc(=O)n([C@@H]3O[C@H](CO)[C@@H](O)[C@H]3O)c2[nH]1]

and prodrugs thereof, (b) ANA975; (c) ANA-025-1; (d) ANA380; (e) the compounds disclosed in references 141 to 143 Compounds containing lipids linked to a phosphate-containing acyclic backbone, such as the TLR4 antagonist E5564 [144,145]:

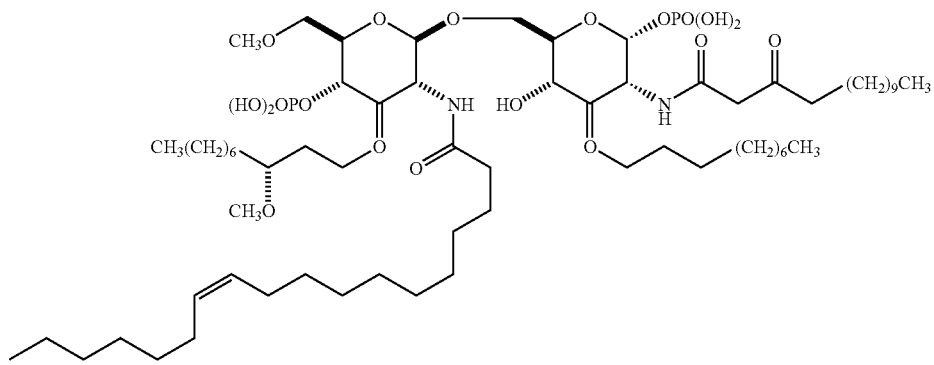

A substituted urea or compound of formula I, II or III, or a salt thereof:
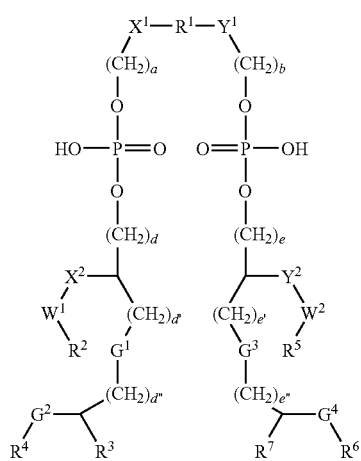
I
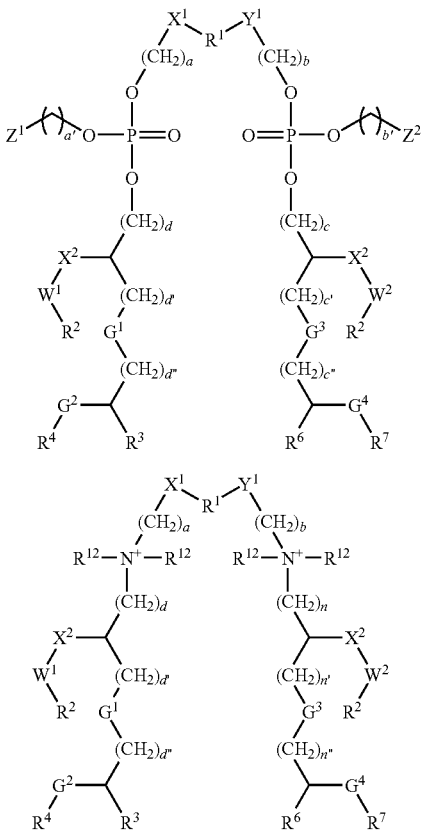
II
III
as defined in reference 146, such as 'ER 803058', 'ER 803732', 'ER 804053', ER 804058', 'ER 804059', 'ER 804442', 'ER 804680', 'ER 804764', ER 803022 or 'ER 804057' e.g.:
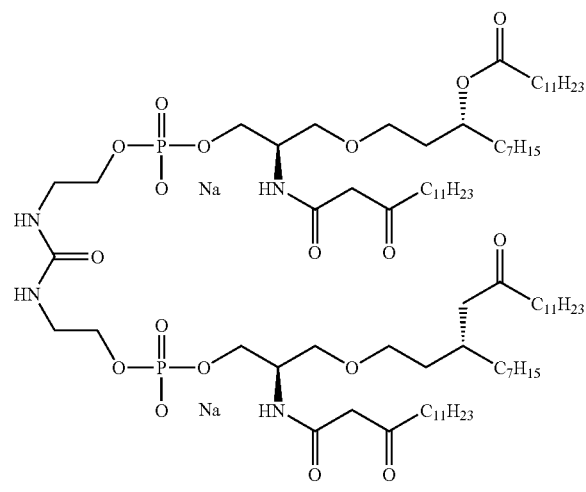
ER804057

-continued

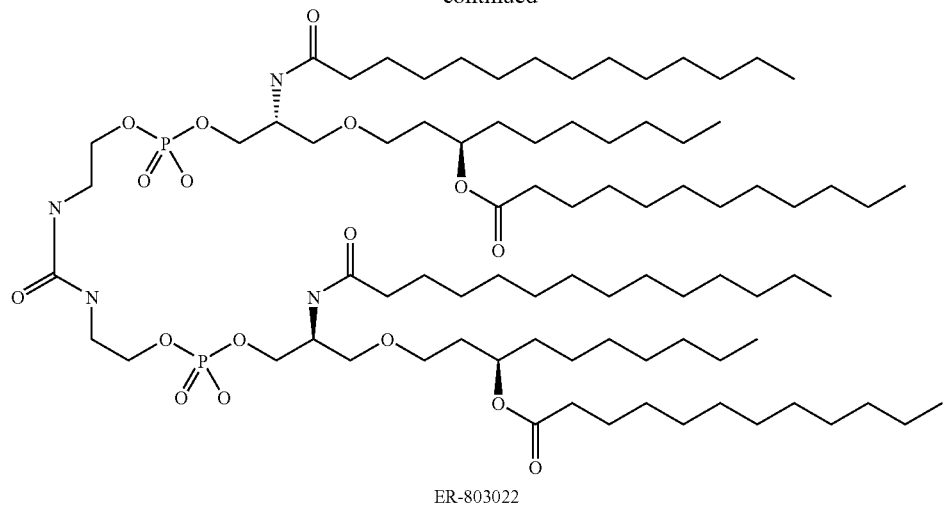

ER-803022

Derivatives of lipid A from *Escherichia coli* such as OM-174 (described in refs. 147 & 148).
Loxoribine (7-allyl-8-oxoguanosine) [149].
Compounds disclosed in reference 150, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [151,152], Hydrapthalamide compounds, Benzophenone compounds, Isoxazole compounds, Sterol compounds, Quinazilinone compounds, Pyrrole compounds [153], Anthraquinone compounds, Quinoxaline compounds, Triazine compounds, Pyrazalopyrimidine compounds, and Benzazole compounds [154].
An aminoalkyl glucosaminide phosphate derivative, such as RC-529 [155,156].
A phosphazene, such as poly[di(carboxylatophenoxy) phosphazene] ("PCPP") as described, for example, in references 157 and 158.

These and other adjuvant-active substances are discussed in more detail in references 162 & 163.

Compositions may include two or more of said adjuvants. Individual adjuvants may preferentially induce either a Th1 response or a Th2 response, and useful combinations of adjuvants can include both a Th2 adjuvant (e.g. an oil-in-water emulsion or an aluminium salt) and a Th1 adjuvant (e.g. 3dMPL, a saponin, or an immunostimulatory oligonucleotide). For example, compositions may advantageously comprise: both an aluminium salt and an immunostimulatory oligodeoxynucleotide; both an aluminium salt and a compound of formula I, II or III; both an oil-in-water emulsion and a compound of formula I, II or III; both an oil-in-water emulsion and an immunostimulatory oligodeoxynucleotide; both an aluminium salt and an α-glycosylceramide; both an oil-in-water emulsion and an α-glycosylceramide; both an oil-in-water emulsion and 3dMPL; both an oil-in-water emulsion and a saponin; etc. Mixtures of 3dMPL and oil-in-water emulsions are very useful.

Preferred adjuvants for use with the invention are oil-in-water emulsions, which have been found to be particularly suitable for use in adjuvanting influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of <1 μm e.g. ≦750 nm, ≦500 nm, ≦400 nm, ≦300 nm, ≦250 nm, ≦220 nm, ≦200 nm, or smaller. These droplet sizes can conveniently be achieved by techniques such as microfluidisation.

Specific oil-in-water emulsion adjuvants useful with the invention include, but are not limited to:

A submicron emulsion of squalene, polysorbate 80, and sorbitan trioleate. The composition of the emulsion by volume can be about 5% squalene, about 0.5% polysorbate 80 and about 0.5% sorbitan trioleate. In weight terms, these ratios become 4.3% squalene, 0.5% polysorbate 80 and 0.48% sorbitan trioleate. This adjuvant is known as 'MF59' [159-161], as described in more detail in Chapter 10 of ref. 162 and chapter 12 of ref. 163. The MF59 emulsion advantageously includes citrate ions e.g. 10 mM sodium citrate buffer.

An emulsion of squalene, a tocopherol, and polysorbate 80. The emulsion may include phosphate buffered saline. It may also include Span 85 (e.g. at 1%) and/or lecithin. These emulsions may have from 2 to 10% squalene, from 2 to 10% tocopherol and from 0.3 to 3% polysorbate 80, and the weight ratio of squalene:tocopherol is preferably ≦1 as this provides a more stable emulsion. Squalene and Tween 80 may be present volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL).

Another useful emulsion of this type may comprise, per human dose, 0.5-10 mg squalene, 0.5-11 mg tocopherol, and 0.1-4 mg polysorbate 80 [164].

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [165] (0.05-1% Thr-MDP, 5% squalane, 2.5% Pluronic L121 and 0.2% polysorbate 80). It can also be used without the Thr-MDP, as in the "AF" adjuvant [166] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [167]. The emulsion may also include one or more of: alditol; a cryoprotective agent (e.g. a sugar, such as dodecylmaltoside and/or sucrose); and/or an alkylpolyglycoside. The emulsion may include a TLR4 agonist [168]. Such emulsions may be lyophilized.

An emulsion of squalene, poloxamer 105 and Abil-Care [169]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 170, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 171, produced by addition of aliphatic amine to desacylsaponin via the carboxyl group of glucuronic acid), dimethyldioctadecylammonium bromide and/or N,N-dioctadecyl-N,N-bis(2-hydroxyethyl)propanediamine.

An emulsion in which a saponin (e.g. QuilA or QS21) and a sterol (e.g. a cholesterol) are associated as helical micelles [172].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [173].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [173].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form, as in the FLUAD™ product. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

After the antigen and adjuvant have been mixed, haemagglutinin antigen will generally remain in aqueous solution but may distribute itself around the oil/water interface. In general, little if any haemagglutinin will enter the oil phase of the emulsion.

Where a composition includes a tocopherol, any of the $\alpha$, $\beta$, $\gamma$, $\delta$, $\epsilon$ or $\xi$ tocopherols can be used, but $\alpha$-tocopherols are preferred. The tocopherol can take several forms e.g. different salts and/or isomers. Salts include organic salts, such as succinate, acetate, nicotinate, etc. D-$\alpha$-tocopherol and DL-$\alpha$-tocopherol can both be used. Tocopherols are advantageously included in vaccines for use in elderly patients (e.g. aged 60 years or older) because vitamin E has been reported to have a positive effect on the immune response in this patient group [174]. They also have antioxidant properties that may help to stabilize the emulsions [175]. A preferred $\alpha$-tocopherol is DL-$\alpha$-tocopherol, and the preferred salt of this tocopherol is the succinate. The succinate salt has been found to cooperate with TNF-related ligands in vivo. Moreover, $\alpha$-tocopherol succinate is known to be compatible with influenza vaccines and to be a useful preservative as an alternative to mercurial compounds [28].

The Child

The invention is used to immunize children against influenza virus infection and/or disease.

The child to be immunized may be aged between 0 months and 72 months, and ideally between 0 months and 36 months. Typically they will be at least 6 months old e.g. in the range 6-72 months old (inclusive) or in the range 6-36 months old (inclusive). Children in these age ranges may in some embodiments be less than 30 months old, or less than 24 months old. For example, a composition may be administered to them at the age of 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 months; or at 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or 71 months; or at 36 or 72 months.

Pharmaceutical Compositions

Compositions of the invention are pharmaceutically acceptable. They may include components in addition to the antigen and adjuvant e.g. they will typically include one or more pharmaceutical carrier(s) and/or excipient(s). A thorough discussion of such components is available in ref. 176.

The composition may include preservatives such as thiomersal or 2-phenoxyethanol. It is preferred, however, that the vaccine should be substantially free from (i.e. less than 5 µg/ml) mercurial material e.g. thiomersal-free [177,178]. Vaccines containing no mercury are more preferred, and $\alpha$-tocopherol succinate can be included as an alternative to mercurial compounds [28]. Preservative-free vaccines are most preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [179], but keeping osmolality in this range is nevertheless preferred.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

Compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10 and polysorbate 80. Other residual components in trace amounts could be antibiotics (e.g. neomycin, kanamycin, polymyxin B).

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children according to the invention.

Compositions and kits are preferably stored at between 2° C. and 8° C. They should not be frozen. They should ideally be kept out of direct light.

The antigen and emulsion in a composition will typically be in admixture, although they may initially be presented in the form of a kit of separate components for extemporaneous admixing. Compositions will generally be in aqueous form when administered to a subject.

Kits of the Invention

Compositions of the invention may be prepared extemporaneously, at the time of delivery, particularly when an adjuvant is being used. Thus the invention provides kits including the various components ready for mixing. The kit allows the adjuvant and the antigen to be kept separately until the time of use. This arrangement can be useful when using an oil-in-water emulsion adjuvant.

The components are physically separate from each other within the kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container.

In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe, such as those disclosed in references 180-187 etc. When the syringe is actuated (e.g. during administration to a patient) then the contents of the two chambers are mixed. This arrangement avoids the need for a separate mixing step at the time of use.

The kit components will generally be in aqueous form. In some arrangements, a component (typically an antigen component rather than an adjuvant component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

Packaging of Compositions or Kit Components

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Useful syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

Compositions of the invention are suitable for administration to human patients, and the invention provides a method of raising an immune response in a patient, comprising the step of administering a composition of the invention to the patient. As described above, the patient is a child.

The invention also provides a kit or composition of the invention for use as a medicament. The invention also provides the medical uses discussed above.

These methods and uses will generally be used to generate an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [188]. Antibody responses are typically measured by hemagglutination inhibition (HI), by microneutralisation (Micro-NT), by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [189-191], oral [192], intradermal [193,194], transcutaneous, transdermal [195], etc.

Preferred compositions of the invention will satisfy 1, 2 or 3 of the CPMP criteria for adult efficacy for each influenza strain, even though they are administered to children. These criteria are: (1) ≧70% seroprotection; (2) ≧40% seroconversion or significant increase; and/or (3) a GMT increase of ≧2.5-fold. In elderly (>60 years), these criteria are: (1) ≧60% seroprotection; (2) ≧30% seroconversion; and/or (3) a GMT increase of ≧2-fold. These criteria are based on open label studies with at least 50 patients.

The invention is particularly useful for raising immune responses that are protective against influenza B virus strains and/or are effective against drifted (mismatched) influenza A virus strains (particularly drifted A/H3N2 strains).

Treatment can be by a single dose schedule or a multiple dose schedule. In any particular influenza season (e.g. in a given 12 month period, typically in autumn or winter) a patient may thus receive a single dose of a composition of the invention or more than one dose (e.g. two doses). A single dose can raise a useful immune response against subtype H3N2 of influenza A virus, whereas two doses may be required to additionally provide a useful immune response against subtype H1N1 of influenza A virus and against influenza B virus. In a multiple dose schedule the various doses may be given by the same or different routes e.g. a parenteral prime and mucosal boost, a mucosal prime and parenteral boost, etc. Typically they will be given by the same route. Multiple doses will typically be administered at least 1 week apart (e.g. about 2 weeks, about 3 weeks, about 4 weeks, about 6 weeks, about 8 weeks, about 12 weeks, about 16 weeks, etc.). Giving two doses separated by from 25-30 days (e.g. 28 days) is particularly useful.

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a pneumococcal conjugate vaccine, etc.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3 (1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

MODES FOR CARRYING OUT THE INVENTION

The Clinical Trial

A phase II clinical trial has been performed in children to assess the immunogenicity, clinical tolerability and safety of an adjuvanted inactivated influenza vaccine in comparison to a non-adjuvanted inactivated vaccine in unprimed healthy children.

Healthy children (6 to <36 months of age) never being previously vaccinated against influenza were invited to participate in the trial. To ensure equal age distribution within this age range, the following subgroups of children were targeted for recruitment: 6-11 months, 12-18 months, 19-24 months, 24-30 months, 31-<36 months. Subjects were randomized to receive one of the two trivalent inactivated influenza vaccines: a subunit vaccine adjuvanted with MF59™ (FLUAD™), or a non-adjuvanted split vaccine (Vaxigrip™). Two doses, 0.25 ml each, were given intramuscularly in the deltoid region of the non-dominant arm or, if the deltoid mass was insufficient, in the anterolateral aspect of the thigh. The second vaccination was four weeks after the first.

The antigenic composition of the two vaccines was in agreement with WHO recommendations for the Northern Hemisphere during the 2006/07 influenza season. For each dose of 0.25 ml vaccines contained 7.5 μg of each of the three influenza antigens: A/New Calcdonia/20/99 (H1N1)-like virus, A/Wisconsin/67/2005 ($H_3N_2$)-like virus, B/Malaysia/2506/2004-like virus.

The study protocol conformed to the ethical guidelines of the 1975 Declaration of Helsinki and Good Clinical Practice and was approved by the Ethics Committee of the University Hospital District of Tampere. Counseling was provided and informed consent was obtained from each child's parents. Exclusion criteria included subjects who had a known allergy to any vaccine component or had experienced any known or suspected neurological reactions following influenza vaccination; had experienced any acute infectious or respiratory disease requiring systemic treatment 30 days before the study start; had experienced a laboratory confirmed influenza disease in the previous 6 months. For each child, a detailed form including demographic and baseline clinical data was completed. Blood samples were obtained before vaccination, four weeks after the first vaccine dose and three weeks after the second one. A fourth blood draw was performed at the study termination, at the end of the six months follow up, to assess immune responses over the duration of an influenza season.

HI antibody titres were measured in all samples against each of the three influenza strains in the vaccine formulation. The following immune parameters were considered: Geometric Mean Titres (GMT) and the corresponding 95% confidence intervals (CI); Geometric Mean Ratio (GMR; ratio of post- to pre-vaccination titre); seroprotection rate, defined as the percentage of subjects achieving an HI titre $\geq 40$; and the percentage of subjects achieving seroconversion (defined as at least a 4-fold increase in HI titre from a non-negative pre-vaccination titre [$\geq 10$] or a rise from $\leq 10$ to $\geq 40$ in those who were seronegative). In addition, the percentage of subjects with HI titres $\geq 160$ was evaluated.

Immediately after any vaccination and for the following seven days, parents were instructed to record solicited local and systemic reactions on a diary card. Body temperature, usage of analgesic/antipyretic medication and any other adverse event were registered on diary cards beginning with the day of vaccination and continuing during the 7 days following each vaccination.

All adverse events (AE) including serious adverse events and those necessitating a physician's consultation, or leading to premature study discontinuation were collected throughout the entire trial.

Data were statistically analysed using the SAS System. The chi-square test was performed to analyze differences between proportions of subjects. Statistical significance between pre- and post-vaccination titres was calculated using the paired Student's t-test. Comparison of different vaccine groups was determined by Student's t-test for unpaired data. A P-value of $<0.05$ was considered to indicate statistical significance.

Results are shown in Table I (after 1 dose) and Table II (after 2 doses). The seroprotection rate is the percentage of children achieving an HI titre $\geq 40$. The seroconversion rate is the percentage of subjects achieving seroconversion or a significant increase in titre (i.e. at least a 4-fold increase in HI titre from a non-negative pre-vaccination titre [$\geq 10$] or a rise from $<10$ to $\geq 40$ in those who were serum-negative). Statistical significance is indicated vs. un-adjuvanted group as: *$p<0.001$; $p<0.01$; *$p<0.05$.

Safety

Overall, 269 children were enrolled and randomized into five age groups to receive the vaccines. Diary cards for local and systemic reactions and AE reports were collected from all 269 children.

There was no statistically significant difference in local and systemic reactions between the two vaccine groups, with the only exception of injection site swelling. All reactions were typically mild or moderate and transient (2-3 days after vaccination). In general, after the second vaccine dose, administered four weeks apart, the trend was for a reduction both in local and systemic reactions recorded, compared to the first vaccination.

The overall analysis of possibly or probably related adverse events, from the study start to end of the six months follow up, found no differences between vaccine groups (21 children in each group, with no severe AE reported). Two children in each group were withdrawn from the trial because of an AE. Two serious adverse events (SAE) were reported during the follow up period in the adjuvanted group (two cases of pneumonia); six SAE were recorded in the unadjuvanted group (two chronic bronchitis, two cases of gastroenteritis, one otitis media and one case of asthma). None of them was judged vaccine-related.

Immunogenicity

Serological analysis was performed on the 222 subjects who completed the full vaccination schedule and had all four sera drawn. The distribution to age subgroups was well matched between groups.

By all comparisons, the immune responses to adjuvanted vaccine were superior to those after unadjuvanted vaccine. Thus adjuvanted influenza vaccines may become the preferred influenza vaccine for young children aged 6 to <36 months.

Baseline GMTs were well balanced between vaccine groups. By all comparisons, immune responses were strongest against H3N2, followed by H1N1 and B, and are presented in this order. The GMTs three weeks after 2nd vaccine dose against H3N2 strain were significantly higher than those recorded versus H1N1 antigen, which in turn were significantly higher than GMTs to influenza B. Furthermore GMTs against H3N2, H1N1 and B, respectively, were significantly higher after vaccination with adjuvanted vaccine than after unadjuvanted vaccine (all comparisons $p<0.001$).

The same trend was observed for immunogenicity results six months after vaccine schedule completion, confirming higher antibody persistence in children vaccinated with adjuvanted vaccine. Although titers declined over this six month period, they were consistently higher in the recipients of adjuvanted vaccine than in recipients of the unadjuvanted vaccine.

Both vaccines yielded high seroprotection rates against H3N2 after two doses of vaccine (100% for adjuvanted vaccine and 99% for unadjuvanted vaccine). However, after one dose, there was a considerable and significant difference in favor of the adjuvanted vaccine, as 91% of the adjuvanted vaccine recipients reached seroprotection level already at this point, compared with only 49% of the unadjuvanted vaccine recipients ($p<0.001$). After six months the seroprotection rate for the adjuvanted vaccine remained at 100%, against 66% for the unadjuvanted vaccine ($p<0.001$), and so the adjuvanted vaccine can offer sustained immune protection throughout an influenza season.

Against H1N1, two doses of adjuvanted vaccine also resulted in 100% seroprotection rate vs. 86% after unadjuvanted vaccine ($p<0.001$). After one dose, the adjuvanted vaccine yielded 51% seroprotection rate vs. only 18% in the unadjuvanted vaccine group ($p<0.001$). After six months the seroprotection rate with the adjuvanted vaccine was again significantly higher ($p<0.001$) than with the unadjuvanted vaccine.

Antibody responses to influenza B were weak after one dose, but after two doses of adjuvanted vaccine 99% of the recipients had seroprotective level of HI antibody vs. only 33% of the recipients of the unadjuvanted vaccine. The lower immunogenicity of influenza B is in accordance with previous studies [13,14]. After six months, the seroprotection rate with the adjuvanted vaccine was again significantly higher ($p<0.001$) than with the unadjuvanted vaccine.

The HI antibody responses against A/H1N1 and A/H3N2 strains after each vaccine were essentially similar in the youngest subgroups i.e. there was no apparent improvement with increasing age, whereas for the B strain a consistent trend of decreasing antibody response was observed in the lower age groups vaccinated with the unadjuvanted vaccine group. This might indicate that the youngest children are responding less to unadjuvanted vaccines even after the second dose, compared to an adjuvanted vaccine. Conversely, the high antibody response to the adjuvanted vaccine could already be seen in the youngest infants, 6 to 11 months old.

Figure 4:
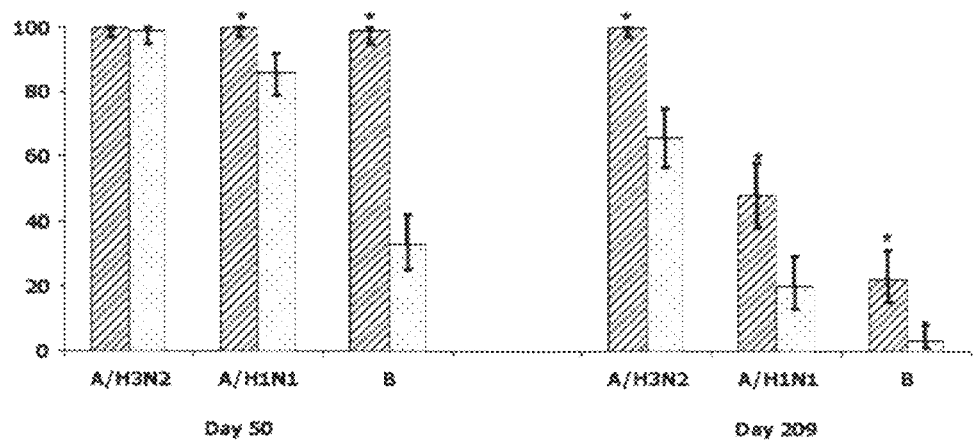
FIG. 4 shows seroprotection rates (% of subjects) in patients at (i) day 50 and (ii) day 209. For each pair of figures, the left-hand bar is the adjuvanted group and the right-hand bar is unadjuvanted. The stars (*) denote P<0.001 versus the unadjuvanted group.

In practice, despite recommendations, young children often only receive one injection of influenza vaccine in a season. Therefore, a vaccine able to elicit higher antibody titers after the first dose may result in improved field efficacy in children. The present study indicated that, for conventional unadjuvanted vaccine, a single dose is not sufficient to induce protective immunity against H1N1 influenza A virus or influenza B virus, and is clearly suboptimal for H3N2 as well. A/H3N2 is currently the most common circulating influenza virus strain, and the adjuvanted vaccine yielded high seroprotection (91%) against this strain even after one dose. FIG. 4 shows that significantly (P<0.001) higher seroprotection rates were obtained with the adjuvanted vaccine for A/H3N2 and A/H1N1 following dose 1, and that this difference was maintained until the end of the study (Day 209). Importantly, the response to H3N2 was also more durable in subjects in the adjuvanted group, with 88% of subjects retaining seroprotective levels of antibody one year after their first influenza vaccination.

Immune Responses Versus Mismatched Strains

As the study used previously-unvaccinated healthy children, the cross-protection potential achieved by the inclusion of adjuvant in the vaccine was directly compared to immunization with a conventional unadjuvanted influenza vaccine. The recent recommendations for strain changes for all three seasonal strains in the vaccine created an opportunity to broadly assess sera from vaccine-immunized subjects for cross reactivity against natural drift strains of influenza virus.

Subjects were immunized with the vaccine recommended for the 2006/07 season, and sera were evaluated against the A/H3N2 and B strains that had been included in the 2005/06 vaccine, before the drift occurred. In addition, heterologous activity was measured against a drifted A/H1N1 strain which was recommended for inclusion in the 2007/08 season. Hence, the changes in all three vaccine strains which were recommended over a two year period offered a unique opportunity to assess the cross-immunogenicity potential achieved by the inclusion of adjuvant in this vaccine-naïve population of young children.

Cross-immunogenicity against mismatched influenza strains was thus evaluated using sera from the children.

Results are in Table III (the * indicates P<0.001).

For both vaccine groups, pre-vaccination GMTs and seroprotection rates were higher for the heterovariant A/H3N2 virus strain than for the other two (A/H1N1 and B) heterologous antigens. Both vaccines induced a significant rise (P<0.001) in GMTs against drifted influenza strains at 3 weeks post-vaccination.

For all three strains, significantly higher GMTs (P<0.001) were recorded in the adjuvanted group, compared to the unadjuvanted group. Furthermore, significantly higher (P<0.001) GMRs were detected in the adjuvanted vaccine group, compared to the unadjuvanted group (A/H3N2: 13 vs. 4.78; A/H1N1: 9.11 vs. 4; B: 2.12 vs. 1.21, respectively).

Satisfactory post-vaccination seroprotection and seroconversion rates were reached in the adjuvanted group against both mismatched A influenza strains in the MF59 group, but not for the B drifted strain. The differences between vaccine groups were statistically significant for all three strains for seroprotection rates, but only for A strains for seroconversion rates.

The analysis of the immunogenicity results according to the Committee for Medicinal Products for Human Use (CHMP; formerly CPMP) criteria for yearly approval of licensed influenza vaccines in healthy adults showed that all 3 criteria were fulfilled for both A antigens in the adjuvanted group, while the unadjuvanted vaccine met only 2 requirements (GMR and seroconversion rate) for the A/H3N2 and only the 1 (mean fold increase in titers) for the A/H1N1 strain.

Thus the inclusion of adjuvant in the influenza vaccine allowed divergent strains, which were sufficiently different to result in a change in recommendation for vaccine strains, to be covered by a protective serum immune response. The drift cover was significantly higher than achieved with an unadjuvanted vaccine. A published multi-year study [196] which evaluated influenza vaccine effectiveness versus antigenic distance of strain mismatches in the vaccine suggests that the cross reactivity achieved with the adjuvanted vaccine would likely have a significant clinical impact.

Observer-Blind Extension Study

Children who had been primed in the initial clinical study were offered to receive a booster dose of the adjuvanted vaccine or unadjuvanted split vaccine one year later. Healthy children (now aged 16 to <48 months) who had been primed with two intramusluclar (IM) doses for the 2006/07 season thus received a third intramuscular dose of the respective vaccine (2007/08 NH vaccine formulation) approximately one year after the first dose (before the start of the 2007/08 season). For the 2007/08 NH season only the A/H1N1-like strain (A/Solomon Islands/3/2006) changed compared with the vaccine formulation of the previous campaign. The third dose of the vaccines was thus like a "booster dose" for the A/H3N2 and B strains, which did not change across the two seasons.

Immunogenicity was evaluated by a haemagglutination inhibition (HI) assay at baseline, before the booster dose, and three weeks after. Seroprotection (SP) was defined as HI titer of 40 or higher and seroconversion (SC) was defined as a $\geq$4-fold increase in HI titre from a pre-vaccination titre $\geq$10 or a rise from <10 to $\geq$40. Solicited local and systemic reactions were monitored immediately after vaccination and for the following seven days. All adverse events (AE) were recorded up to 3 weeks after injection.

Overall, 89 children took part in this extension study. Both vaccines were confirmed to be safe and well tolerated after a second seasonal vaccination. Mild solicited reactions were more frequently recorded in the adjuvanted group, whereas AEs were more common in the split group.

Baseline HI antibody titers, SP rates and SC rates were higher in the adjuvanted group compared with the split group. The difference in persistence of antibody titers, approximately one year after priming, was particularly evident against the A/H3N2 strain (adjuvanted 88% SP vs. unadjuvanted 40% SP, p<0.001). For both vaccines the immune responses after vaccination were strongest against A/H3N2, followed by A/H1N1 and B. The adjuvanted vaccine induced significantly higher GMTs than the unadjuvanted vaccine against all three vaccine strains. All subjects in the adjuvanted group achieved SP against all three vaccine strains whereas split vaccine conferred seroprotection in the 68% of children against the B antigen (p<0.001). The same trend was observed for the percentage of children achieving SC, with the greatest difference between groups being for the B strain (98% in the adjuvanted group vs. 68% in the unadjuvanted group, p<0.001). Results are in Table IV.

After the second year booster dose, seroprotection against the B strain in younger children remained at less than 50% in the unadjuvanted vaccine group compared with 100% in the adjuvanted group.

Thus the adjuvanted influenza vaccine was confirmed to be safe and well tolerated following a second consecutive seasonal vaccination. Baseline HI antibody titers, were consistently higher in children receiving adjuvanted vaccine, confirming a better persistence of immunogenicity after priming than with a conventional vaccine. The adjuvanted vaccine induced higher increases in immune responses three weeks after vaccination, especially in the youngest children (<3 years of age) and against the B influenza strain, which is epidemiologically relevant in the pediatric population. These data further support the use of adjuvanted vaccine as a safe and very immunogenic influenza vaccine for children.

The results of this extension study, performed to mimic the ideal field conditions of consecutive seasonal vaccinations, further support the use of adjuvanted vaccines as a highly immunogenic and well-tolerated way for actively immunizing against seasonal influenza in healthy children.

It will be understood that the invention has been described by way of example only and modifications may be made whilst remaining within the scope and spirit of the invention.

[01] *Vaccines*. (eds. Plotkin & Orenstein). 4th edition, 2004, ISBN: 0-7216-9688-0.
[02] Neuzil et al. (2000) *N Engl J Med* 342:225-31.
[03] Peltola et al. (2003) *Clin Infect Dis* 36:299-305.
[04] Heikkinen et al. (2004) *J Infect Dis* 190:1369-73.
[05] Izurieta et al. (2000) *N Engl J Med* 342:232-39.
[06] Poehling et al. (2006) *N Engl J Med* 355:31-40.
[07] Iskander et al. (2007) *Current Opin Infect Dis* 20:259-263.
[08] Ghendon et al. (2006) *Epidemiol Infect* 134:71-78.
[09] Principi et al. (2003) *Pediatr Infect Dis J* 22(10 Suppl): S207-10.
[10] Fiore et al. (2008) *MMWR Early Release* 2008; 57:1-60.
[11] ECDC. Technical report on the scientific panel on Vaccines and immunization. Infant and children seasonal immunization against influenza on a routine basis during inter-pandemic period. Stockholm, January 2007.
[12] Demicheli et al. 2006) The Cochrane collaboration. *Vaccines for preventing influenza in healthy children* (Review). The Cochrane library, 2006, issue 3. Available at: www.thecochranelibrary.com
[13] Walter et al. (2006) *Pediatrics* 1118:e570-78.
[14] Mitchell et al. (2005) *Pediatr Infect Dis J* 10:925-26.
[15] Centers for Disease Control and Prevention. Prevention and control of influenza. *MMWR Early Release* 2007; 56 June 29:1-53.
[16] Treanor (2004). *N Engl J. Med.* 350(3): 218-20.
[17] Ferguson, et al. (2003). *Nature.* 422(6930): 428-33.
[18] Koelle et al. (2006). *Science* 314(5807): 1898-903.
[19] Skowronski et al. (2007). *Vaccine* 25(15): 2842-51.
[20] Louie et al. (2006). *Pediatrics.* 117(4): e610-8.
[21] WO96/37624.
[22] WO98/46262.
[23] WO2007/085969.
[24] WO02/28422.
[25] WO02/067983.
[26] WO02/074336.
[27] WO01/21151.
[28] WO02/097072.
[29] WO2005/113756.
[30] Huckriede et al. (2003) *Methods Enzymol* 373:74-91.
[31] Treanor et al. (1996) *J Infect Dis* 173:1467-70.
[32] Keitel et al. (1996) *Clin Diagn Lab Immunol* 3:507-10.
[33] Rota et al. (1992) *J Gen Virol* 73:2737-42.
[34] GenBank sequence GI:325176.
[35] Hoffmann et al. (2002) *Vaccine* 20:3165-3170.
[36] Subbarao et al. (2003) *Virology* 305:192-200.
[37] Liu et al. (2003) *Virology* 314:580-590.
[38] Ozaki et al. (2004) *J. Virol.* 78:1851-1857.
[39] Webby et al. (2004) *Lancet* 363:1099-1103.
[40] WO00/60050.
[41] WO01/04333.
[42] U.S. Pat. No. 6,649,372.
[43] Neumann et al. (2005) *Proc Natl Acad Sci USA* 102: 16825-9.
[44] WO2006/067211.
[45] WO01/83794.
[46] Hoffmann et al. (2000) *Virology* 267(2):310-7.
[47] Herlocher et al. (2004) *J Infect Dis* 190(9):1627-30.
[48] Le et al. (2005) *Nature* 437(7062):1108.
[49] Kistner et al. (1998) *Vaccine* 16:960-8.
[50] Kistner et al. (1999) *Dev Biol Stand* 98:101-110.
[51] Bruhl et al. (2000) *Vaccine* 19:1149-58.
[52] Pau et al. (2001) *Vaccine* 19:2716-21.
[53] http://www.atcc.org/
[54] http://locus. umdnj. edu/
[55] WO03/076601.
[56] WO2005/042728.
[57] WO03/043415.
[58] WO01/85938.
[59] WO2006/108846.
[60] WO97/37000.
[61] Brands et al. (1999) *Dev Biol Stand* 98:93-100.
[62] Halperin et al. (2002) *Vaccine* 20: 1240-7.
[63] Tree et al. (2001) *Vaccine* 19:3444-50.
[64] EP-A-1260581 (WO01/64846).
[65] WO2006/071563.
[66] WO2005/113758.
[67] WO97/37001.
[68] WO2006/027698.
[69] EP B 0870508.
[70] U.S. Pat. No. 5,948,410.
[71] Lundblad (2001) *Biotechnology and Applied Biochemistry* 34:195-197.
[72] Guidance for Industry: Bioanalytical Method Validation. U.S. Department of Health and Human Services Food and Drug Administration Center for Drug Evaluation and Research (CDER) Center for Veterinary Medicine (CVM). May 2001.
[73] Ji et al. (2002) *Biotechniques.* 32:1162-7.
[74] Briggs (1991) *J Parenter Sci Technol.* 45:7-12.
[75] Lahijani et al. (1998) *Hum Gene Ther.* 9:1173-80.
[76] Lokteff et al. (2001) *Biologicals.* 29:123-32.
[77] U.S. Pat. No. 6,355,271.
[78] WO00/23105.
[79] U.S. Pat. No. 5,057,540.
[80] WO96/33739.
[81] EP A 0109942.
[82] WO96/11711.
[83] WO00/07621.
[84] Barr et al. (1998) *Advanced Drug Delivery Reviews* 32:247 271.
[85] Sjolanderet et al. (1998) *Advanced Drug Delivery Reviews* 32:321 338.
[86] Pizza et al. (2000) *Int J Med Microbiol* 290:455-461.
[87] Tebbey et al. (2000) *Vaccine* 18:2723-34.
[88] WO95/17211.
[89] WO98/42375.
[90] Singh et al] (2001) *J Cont Release* 70:267-276.
[91] WO99/27960.
[92] U.S. Pat. No. 6,090,406
[93] U.S. Pat. No. 5,916,588
[94] EP A 0626169.
[95] Dyakonova et al. (2004) *Int Immunopharmacol* 4(13): 1615-23.
[96] FR-2859633.
[97] Signorelli & Hadden (2003) *Int Immunopharmacol* 3(8): 1177-86.
[98] WO2004/064715.

[99] De Libero et al, *Nature Reviews Immunology*, 2005, 5: 485-496
[100] U.S. Pat. No. 5,936,076.
[101] Oki et al, *J. Clin. Investig.*, 113: 1631-1640
[102] US2005/0192248
[103] Yang et al, *Angew. Chem. Int. Ed.*, 2004, 43: 3818-3822
[104] WO2005/102049
[105] Goff et al, *J. Am. Chem., Soc.*, 2004, 126: 13602-13603
[106] WO03/105769
[107] Cooper (1995) *Pharm Biotechnol* 6:559-80.
[108] Kandimalla et al. (2003) *Nucleic Acids Research* 31:2393-2400.
[109] WO02/26757.
[110] WO99/62923.
[111] Krieg (2003) *Nature Medicine* 9:831-835.
[112] McCluskie et al. (2002) *FEMS Immunology and Medical Microbiology* 32:179-185.
[113] WO98/40100.
[114] U.S. Pat. No. 6,207,646.
[115] U.S. Pat. No. 6,239,116.
[116] U.S. Pat. No. 6,429,199.
[117] Kandimalla et al. (2003) *Biochemical Society Transactions* 31 (part 3):654-658.
[118] Blackwell et al. (2003) *J Immunol* 170:4061-4068.
[119] Krieg (2002) *Trends Immunol* 23:64-65.
[120] WO01/95935.
[121] Kandimalla et al. (2003) *BBRC* 306:948-953.
[122] Bhagat et al. (2003) *BBRC* 300:853-861.
[123] WO03/035836.
[124] WO01/22972.
[125] Schellack et al. (2006) *Vaccine* 24:5461-72.
[126] Myers et al. (1990) pages 145-156 of Cellular and molecular aspects of endotoxin reactions.
[127] Ulrich (2000) Chapter 16 (pages 273-282) of reference 163.
[128] Johnson et al. (1999) *J Med Chem* 42:4640-9.
[129] Baldrick et al. (2002) *Regulatory Toxicol Pharmacol* 35:398-413.
[130] WO 94/21292.
[131] U.S. Pat. No. 4,680,338.
[132] U.S. Pat. No. 4,988,815.
[133] WO92/15582.
[134] Stanley (2002) *Clin Exp Dermatol* 27:571-577.
[135] Wu et al. (2004) *Antiviral Res.* 64(2):79-83.
[136] Vasilakos et al. (2000) *Cell Immunol.* 204(1):64-74.
[137] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[138] Jones (2003) *Curr Opin Investig Drugs* 4:214-218.
[139] WO2004/060308.
[140] WO2004/064759.
[141] U.S. Pat. No. 6,924,271.
[142] US2005/0070556.
[143] U.S. Pat. No. 5,658,731.
[144] Wong et al. (2003) *J Clin Pharmacol* 43(7):735-42.
[145] US2005/0215517.
[146] WO03/011223.
[147] Meraldi et al. (2003) *Vaccine* 21:2485-2491.
[148] Pajak et al. (2003) *Vaccine* 21:836-842.
[149] U.S. Pat. No. 5,011,828.
[150] WO2004/87153.
[151] U.S. Pat. No. 6,605,617.
[152] WO02/18383.
[153] WO2004/018455.
[154] WO03/082272.
[155] Johnson et al. (1999) *Bioorg Med Chem Lett* 9:2273-2278.
[156] Evans et al. (2003) *Expert Rev Vaccines* 2:219-229.
[157] Andrianov et al. (1998) *Biomaterials* 19:109-115.
[158] Payne et al. (1998) *Adv Drug Delivery Review* 31:185-196.
[159] WO90/14837.
[160] Podda & Del Giudice (2003) *Expert Rev Vaccines* 2:197-203.
[161] Podda (2001) *Vaccine* 19: 2673-2680.
[162] *Vaccine Design The Subunit and Adjuvant Approach* (eds. Powell & Newman) Plenum Press 1995 (ISBN 0-306-44867-X).
[163] *Vaccine Adjuvants Preparation Methods and Research Protocols* (Volume 42 of *Methods in Molecular Medicine* series). ISBN: 1-59259-083-7. Ed. O'Hagan.
[164] WO2008/043774.
[165] Allison & Byars (1992) *Res Immunol* 143:519-25.
[166] Hariharan et al. (1995) *Cancer Res* 55:3486-9.
[167] US 2007/014805.
[168] US-2007/0191314.
[169] Suli et al. (2004) *Vaccine* 22(25-26):3464-9.
[170] WO95/11700.
[171] U.S. Pat. No. 6,080,725.
[172] WO2005/097181.
[173] WO2006/113373.
[174] Han et al. (2005) *Impact of Vitamin E on Immune Function and Infectious Diseases in the Aged at Nutrition*, Immune functions and Health EuroConference, Paris, 9-10 Jun. 2005.
[175] U.S. Pat. No. 6,630,161.
[176] Gennaro (2000) *Remington: The Science and Practice of Pharmacy.* 20th edition, ISBN: 0683306472.
[177] Banzhoff (2000) *Immunology Letters* 71:91-96.
[178] WO02/097072.
[179] Nony et al. (2001) *Vaccine* 27:3645-51.
[180] WO2005/089837.
[181] U.S. Pat. No. 6,692,468.
[182] WO00/07647.
[183] WO99/17820.
[184] U.S. Pat. No. 5,971,953.
[185] U.S. Pat. No. 4,060,082.
[186] EP A 0520618.
[187] WO98/01174.
[188] Potter & Oxford (1979) *Br Med Bull* 35: 69-75.
[189] Greenbaum et al. (2004) *Vaccine* 22:2566-77.
[190] Zurbriggen et al. (2003) *Expert Rev Vaccines* 2:295-304.
[191] Piascik (2003) *J Am Pharm Assoc (Wash DC).* 43:728-30.
[192] Mann et al. (2004) *Vaccine* 22:2425-9.
[193] Halperin et al. (1979) *Am J Public Health* 69:1247-50.
[194] Herbert et al. (1979) *J Infect Dis* 140:234-8.
[195] Chen et al. (2003) *Vaccine* 21:2830-6.
[196] Gupta, V., D. J. Earl, et al. (2006). "Quantifying influenza Vaccine efficacy and antigenic distance." *Vaccine.* 24(18): 3881-8 Epub 2006 Jan. 19.

TABLE I

| Strain | Immunogenicity End points | Age Groups | | | | | |
|---|---|---|---|---|---|---|---|
| | | up to 11 months | | 12-17 months | | 18-23 months | |
| | | Adjuv N = 19 | Unadjuv N = 26 | Adjuv N = 22 | Unadjuv N = 15 | Adjuv N = 22 | Unadjuv N = 26 |
| A/H3N2 | GMT | 77** | 27 | 88** | 28 | 94 | 48 |
| | (95% CI) | (45-131) | (17-42) | (56-138) | (16-48) | (48-183) | (26-89) |
| | GMR | 15* | 3.79 | 14** | 5.53 | 11** | 4.69 |
| | (95% CI) | (11-22) | (2.80-5.13) | (9.56-20) | (3.59-8.52) | (6.95-16) | (3.18-6.93) |
| | Seroprotection | 95* | 38 | 91*** | 53 | 91*** | 62 |
| | % (95% CI) | (74-100) | (20-59) | (71-99) | (27-79) | (71-99) | (41-80) |
| | HI titre ≧ 160 | 16 | 8 | 27 | 0 | 27 | 19 |
| | % (95% CI) | (3-40) | (1-25) | (11-50) | (0-22) | (11-50) | (7-39) |
| | Seroconversion | 95* | 35 | 86 | 53 | 86*** | 54 |
| | % (95% CI) | (74-100) | (17-56) | (65-97) | (27-79) | (65-97) | (33-73) |
| A/H1N1 | GMT | 30*** | 13 | 27** | 14 | 25 | 27 |
| | (95% CI) | (18-49) | (8.62-20) | (20-36) | (9.40-19) | (12-50) | (14-51) |
| | GMR | 5.98* | 2.29 | 5.31** | 2.70 | 4.99*** | 2.90 |
| | (95% CI) | (4.28-8.35) | (1.72-3.04) | (3.94-7.16) | (1.88-3.88) | (3.52-7.06) | (2.11-4.00) |
| | Seroprotection | 47*** | 15 | 41 | 13 | 45 | 19 |
| | % (95% CI) | (24-71%) | (4-35%) | (21-64%) | (2-40) | (24-68) | (7-39) |
| | HI titre ≧ 160 | 0 | 4 | 0 | 0 | 0 | 15 |
| | % (95% CI) | (0-18) | (0.097-20) | (0-15) | (0-22) | (0-15) | (4-35) |
| | Seroconversion | 47*** | 15 | 41 | 13 | 45*** | 15 |
| | % (95% CI) | (24-71) | (4-35) | (21-64) | (2-40) | (24-68) | (4-35) |
| B | GMT | 7.47 | 5.00 | 7.30*** | 5.24 | 5.33 | 6.36 |
| | (95% CI) | (5.10-11) | (3.61-6.92) | (6.02-8.85) | (4.15-6.61) | (3.86-7.34) | (4.73-8.54) |
| | GMR | 1.29 | 1.00 | 1.46*** | 1.05 | 1.07 | 1.21 |
| | (95% CI) | (1.06-1.57) | (0.84-1.18) | (1.20-1.77) | (0.83-1.32) | (0.83-1.36) | (0.96-1.51) |
| | Seroprotection | 5 | 0 | 0 | 0 | 0 | 4 |
| | % (95% CI) | (0-26) | (0-13) | (0-15) | (0-22) | (0-15) | (0.097-20) |
| | HI titre ≧ 160 | 5 | 0 | 0 | 0 | 0 | 4 |
| | % (95% CI) | (0-26) | (0-13) | (0-15) | (0-22) | (0-15) | (0.097-20) |
| | Seroconversion | 5 | 0 | 0 | 0 | 0 | 4 |
| | % (95% CI) | (0-26%) | (0-13%) | (0-15%) | (0-22%) | (0-15%) | (0.097-20%) |

| Strain | Immunogenicity End points | Age Groups | | | | | |
|---|---|---|---|---|---|---|---|
| | | 24-29 months | | 30-35 months | | Overall Population | |
| | | Adjuv N = 18 | Unadjuv N = 30 | Adjuv N = 23 | Unadjuv N = 21 | Adjuv N = 104 | Unadjuv N = 118 |
| A/H3N2 | GMT | 145** | 30 | 111 | 71 | 100* | 38 |
| | (95% CI) | (67-313) | (17-55) | (48-261) | (29-174) | (74-135) | (28-50) |
| | GMR | 11* | 4.09 | 11* | 3.93 | 12* | 4.28 |
| | (95% CI) | (7.55-15) | (3.13-5.35) | (7.98-16) | (2.77-5.58) | (10-14) | (3.69-4.97) |
| | Seroprotection | 89** | 47 | 91** | 48 | 91* | 49 |
| | % (95% CI) | (65-99) | (28-66) | (72-99) | (26-70) | (84-96) | (40-59) |
| | HI titre ≧ 160 | 33 | 10 | 22 | 33 | 25*** | 14 |
| | % (95% CI) | (13-59) | (2-27) | (7-44) | (15-57) | (17-34) | (9-22) |
| | Seroconversion | 89** | 47 | 91* | 38 | 89* | 45 |
| | % (95% CI) | (65-99) | (28-66) | (72-99) | (18-62) | (82-95) | (36-54) |
| A/H1N1 | GMT | 48** | 12 | 47 | 25 | 34* | 17 |
| | (95% CI) | (25-91) | (7.04-19) | (23-95) | (12-52) | (26-44) | (13-21) |
| | GMR | 6.60* | 2.02 | 5.74 | 3.81 | 5.66* | 2.61 |
| | (95% CI) | (4.57-9.53) | (1.52-2.69) | (3.90-8.46) | (2.54-5.71) | (4.85-6.60) | (2.26-3.02) |
| | Seroprotection | 56** | 13 | 65*** | 29 | 51* | 18 |
| | % (95% CI) | (31-78) | (4-31) | (43-84) | (11-52) | (41-61) | (11-26) |
| | HI titre ≧ 160 | 11 | 3 | 13 | 10 | 5 | 7 |
| | % (95% CI) | (1-35) | (0.084-17) | (3-34) | (1-30) | (2-11) | (3-13) |
| | Seroconversion | 56** | 13 | 65*** | 29 | 51* | 17 |
| | % (95% CI) | (31-78) | (4-31) | (43-84) | (11-52) | (41-61) | (11-25) |
| B | GMT | 15*** | 5.74 | 8.86 | 6.73 | 8.11** | 5.79 |
| | (95% CI) | (8.01-28) | (3.54-9.33) | (5.78-14) | (4.30-11) | (6.75-9.74) | (4.87-6.88) |
| | GMR | 2.47*** | 1.12 | 1.62 | 1.22 | 1.50** | 1.12 |
| | (95% CI) | (1.48-4.13) | (0.75-1.67) | (1.23-2.13) | (0.91-1.62) | (1.31-1.72) | (0.98-1.27) |
| | Seroprotection | 17 | 3 | 4 | 5 | 5 | 3 |
| | % (95% CI) | (4-41) | (0.084-17) | (0-22) | (0-24) | (2-11) | (1-7) |
| | HI titre ≧ 160 | 17 | 3 | 4 | 5 | 5 | 3 |
| | % (95% CI) | (4-41) | (0.084-17) | (0-22) | (0-24) | (2-11) | (1-7) |
| | Seroconversion | 17 | 3 | 4 | 5 | 5 | 3 |
| | % (95% CI) | (4-41%) | (0.084-17%) | (0-22%) | (0-24%) | (2-11%) | (1-7%) |

TABLE II

| | | Age Groups | | | | | |
|---|---|---|---|---|---|---|---|
| | | up to 11 months | | 12-17 months | | 18-23 months | |
| Strain | Immunogenicity End points | Adjuv N = 19 | Split N = 26 | Adjuv N = 22 | Unadjuv N = 15 | Adjuv N = 22 | Unadjuv N = 26 |
| A/H3N2 | GMT | 514* | 135 | 381** | 156 | 521*** | 259 |
| | (95% CI) | (326-811) | (91-199) | (263-531) | (100-245) | (330-824) | (170-394) |
| | GMR | 103* | 19 | 59*** | 31 | 59*** | 25 |
| | (95% CI) | (66-160) | (13-28) | (40-87) | (20-50) | (35-99) | (16-40) |
| | Seroprotection[a] | 100 | 96 | 100 | 100 | 100 | 100 |
| | % (95% CI) | (82-100) | (80-100) | (85-100) | (78-100) | (85-100) | (87-100) |
| | HI titre ≧ 160 | 100* | 54 | 95*** | 67 | 95** | 62 |
| | % (95% CI) | (82-100) | (33-73) | (77-100) | (38-88) | (77-100) | (41-80) |
| | Seroconversion[b] | 100 | 92 | 100 | 100 | 95 | 96 |
| | % (95% CI) | (82-100) | (75-99) | (85-100) | (78-100) | (77-100) | (80-100) |
| A/H1N1 | GMT | 218* | 76 | 163** | 80 | 165 | 123 |
| | (95% CI) | (144-332) | (53-108) | (120-221) | (55-116) | (97-282) | (75-201) |
| | GMR | 44* | 13 | 33** | 16 | 33* | 13 |
| | (95% CI) | (30-63) | (9.69-18) | (22-44) | (11-23) | (23-47) | (9.68-18) |
| | Seroprotection[a] | 100 | 85 | 100 | 100 | 100 | 88 |
| | % (95% CI) | (82-100) | (65-96) | (85-100) | (78-100) | (85-100) | (70-98) |
| | HI titre ≧ 160 | 79* | 27 | 68** | 27 | 64*** | 35 |
| | % (95% CI) | (54-94) | (12-48) | (45-86) | (8-55) | (41-83) | (17-56) |
| | Seroconversion[b] | 100 | 85 | 100 | 100 | 100 | 85 |
| | % (95% CI) | (82-100) | (65-96) | (85-100) | (78-100) | (85-100) | (65-96) |
| B | GMT | 96* | 11 | 95* | 19 | 80* | 24 |
| | (95% CI) | (66-140) | (7.65-15) | (66-136) | (12-29) | (52-124) | (16-36) |
| | GMR | 17* | 2.11 | 19* | 3.73 | 16* | 4.57 |
| | (95% CI) | (12-23) | (1.6-2.79) | (13-27) | (2.42-5.76) | (11-24) | (3.15-6.63) |
| | Seroprotection[a] | 100* | 12 | 95* | 27 | 100* | 38 |
| | % (95% CI) | (82-100) | (2-30) | (77-100) | (8-55) | (85-100) | (20-59) |
| | HI titre ≧ 160 | 26** | 0 | 36** | 0 | 32 | 8 |
| | % (95% CI) | (9-51) | (0-13) | (17-59) | (0-22) | (14-55) | (1-25) |
| | Seroconversion[b] | 100* | 12 | 95* | 27 | 100* | 38 |
| | % (95% CI) | (82-100) | (2-30) | (77-100) | (8-55) | (85-100) | (20-59) |

| | | Age Groups | | | | | |
|---|---|---|---|---|---|---|---|
| | | 24-29 months | | 30-35 months | | Overall Population | |
| Strain | Immunogenicity End points | Adjuv N = 18 | Unadjuv N = 30 | Adjuv N = 23 | Unadjuv N = 21 | Adjuv N = 104 | Unadjuv N = 118 |
| A/H3N2 | GMT | 518* | 168 | 630 | 315 | 507* | 195 |
| | (95% CI) | (324-828) | (116-241) | (362-1098) | (176-563) | (412-623) | (160-237) |
| | GMR | 38 | 23 | 63* | 17 | 61* | 22 |
| | (95% CI) | (23-62) | (16-33) | (40-99) | (11-28) | (50-75) | (18-27) |
| | Seroprotection[a] | 100 | 100 | 100 | 100 | 100 | 99 |
| | % (95% CI) | (81-100) | (88-100) | (85-100) | (84-100) | (97-100) | (95-100) |
| | HI titre ≧ 160 | 100** | 70 | 100** | 71 | 98* | 64 |
| | % (95% CI) | (81-100) | (51-85) | (85-100) | (48-89) | (93-100) | (55-73) |
| | Seroconversion[b] | 94 | 100 | 100 | 90 | 98 | 96 |
| | % (95% CI) | (73-100) | (88-100) | (85-100) | (70-99) | (93-100) | (90-99) |
| A/H1N1 | GMT | 205* | 69 | 240 | 133 | 195* | 92 |
| | (95% CI) | (134-316) | (49-96) | (137-421) | (74-240) | (159-240) | (76-111) |
| | GMR | 29* | 12 | 30 | 20 | 33* | 14 |
| | (95% CI) | (21-39) | (9.39-15) | (20-44) | (13-31) | (28-38) | (12-17) |
| | Seroprotection[a] | 100 | 83 | 100*** | 81 | 100* | 86 |
| | % (95% CI) | (87-100) | (65-94) | (85-100) | (58-95) | (97-100) | (79-92) |
| | HI titre ≧ 160 | 72* | 17 | 70 | 52 | 70* | 31 |
| | % (95% CI) | (47-90) | (6-35) | (47-87) | (30-74) | (60-79) | (22-40) |
| | Seroconversion[b] | 100 | 83 | 100*** | 81 | 100* | 86 |
| | % (95% CI) | (82-100) | (65-94) | (85-100) | (58-95) | (97-100) | (78-91) |
| B | GMT | 129* | 23 | 140* | 33 | 105* | 20 |
| | (95% CI) | (84-199) | (17-33) | (95-205) | (22-50) | (88-127) | (17-24) |
| | GMR | 21* | 4.59 | 26* | 6.05 | 19* | 3.95 |
| | (95% CI) | (14-32) | (3.39-6.22) | (18-36) | (4.23-8.64) | (16-23) | (3.38-4.62) |
| | Seroprotection[a] | 100* | 33 | 100* | 57 | 99* | 33 |
| | % (95% CI) | (81-100) | (17-53) | (85-100) | (34-78) | (95-100) | (25-42) |
| | HI titre ≧ 160 | 56* | 3 | 57** | 14 | 41* | 5 |
| | % (95% CI) | (31-78) | (0.084-17) | (34-77) | (3-36) | (32-51) | (2-11) |
| | Seroconversion[b] | 100* | 33 | 100* | 57 | 99* | 33 |
| | % (95% CI) | (81-100) | (17-53) | (85-100) | (34-78) | (95-100) | (25-42) |

TABLE III

|  | Adjuvanted | | | Unadjuvanted | | |
| --- | --- | --- | --- | --- | --- | --- |
|  | A/H3N2 | A/H1N1 | B | A/H3N2 | A/H1N1 | B |
| Pre-vaccination GMT | 8.08 | 5.99 | 5.2 | 8.53 | 6.55 | 5 |
| Post-vaccination GMT | 106* | 55* | 11* | 41 | 26 | 6.07 |
| GMR | 13* | 9.11* | 2.12* | 4.78 | 4 | 1.21 |

TABLE IV (Geometric Mean Ratios, Seroprotection and Seroconversion Rates by Vaccine and Age Group)

Number of Subjects (%) and (95% CI)
Strain

|  |  | A/H1N1 | | A/H3N2 | | B | |
| --- | --- | --- | --- | --- | --- | --- | --- |
|  |  | Vaccine Group | | | | | |
|  |  | Sub/MF59 | split | Sub/MF59 | Split | Sub/MF59 | split |
|  | Population | N = 41 | N = 40 | N = 41 | N = 40 | N = 41 | N = 40 |
| Overall | SP[a] (day 1) | 6 (15%) (6, 29) | 2 (5%) (1, 17) | 36 (88%)* (74-96) | 16 (40%) (25-57) | 4 (10%) (3-23) | 0 (0%) (0-9) |
|  | SP[a] (day 22) | 41 (100%) (91-100) | 40 (100%) (91-100) | 41 (100%) (91-100) | 40 (100%) (91-100) | 41 (100%)* (91-100) | 27 (68%) (51-81) |
|  | GMR (day 22/day 1) | 91 (59-140) | 52 (35-79) | 17 (12-24) | 12 (8.08-18) | 18* (14-24) | 8.14 (5.7-12) |
|  | Serocon. rate[b] (day 22) | 39 (95%) (83-99) | 38 (95%) (83-99) | 40 (98%) (87-100) | 34 (85%) (70-94) | 40 (98%)* (87-100) | 27 (68%) (51-81) |
|  |  | N = 23 | N = 20 | N = 23 | N = 20 | N = 23 | N = 20 |
| <3 years | SP[a] (day 1) | 2 (9%) (1-28) | 1 (5%) (0-25) | 22 (96%)* (78-100) | 10 (50%) (27-73) | 1 (4%) (0-22) | 0 (0%) (0-17) |
|  | SP[a] (day 22) | 23 (100%) (85-100) | 20 (100%) (83-100) | 23 (100%) (85-100) | 20 (100%) (83-100) | 23 (100%)* (85-100) | 9 (45%) (23-68) |
|  | GMR (day 22/day 1) | 122** (77-194) | 43 (25-75) | 17*** (11-24) | 7.86 (5.01-12) | 19* (14-27) | 4.14 (2.7-6.35) |
|  | Serocon. rate[b] (day 22) | 23 (100%) (85-100) | 19 (95%) (75-100) | 23 (100%) (85-100) | 17 (85%) (62-97) | 22 (96%)* (78-100) | 9 (45%) (23-68) |
|  |  | N = 18 | N = 20 | N = 18 | N = 20 | N = 18 | N = 20 |
| ≧3 years | SP[a] (day 1) | 4 (22%) (6-48) | 1 (5%) (0-25) | 14 (78%)* (52-94) | 6 (30%) (12-54) | 3 (17%) (4-41) | 0 (0%) (0-17) |
|  | SP[a] (day 22) | 18 (100%) (81-100) | 20 (100%) (83-100) | 18 (100%) (81-100) | 20 (100%) (83-100) | 18 (100%) (81-100) | 18 (90%) (68-99) |
|  | GMR (day 22/day 1) | 63 (28-141) | 64 (34-121) | 18 (9.58-34) | 19 (9.68-36) | 17 (11-26) | 16 (11-24) |
|  | Serocon. rate[b] (day 22) | 16 (89%) (65-99) | 19 (95%) (75-100) | 17 (94%) (73-100) | 17 (85%) (62-97) | 18 (100%) (81-100) | 18 (90%) (68-99) |

[a]Seroprotection: HI titers ≧ 40 IU;
[b]Seroconversion rate: seroconversion and/or significant increase;
Seroconversion - negative pre-vaccination serum (i.e., HI titer < 10 IU) and post-vaccination HI titer ≧ 40 IU and Significant increase - at least 4-fold increase in HI titers in subjects who were positive pre-vaccination (i.e., HI titer ≧ 10 IU).
*p < 0.001;
**p < 0.01;
***p < 0.05 vs. split group

The invention claimed is:

1. A method for raising an immune response to an influenza B virus strain in a human child of up to 72 months of age, comprising a step of administering to the child an immunogenic composition comprising: (i) an influenza B virus strain antigen; and (ii) an adjuvant, wherein the adjuvant comprises an oil-in-water emulsion in which the majority of oil droplets have a diameter of less than 1 μm and the oil droplets comprise squalene.

2. The method of claim 1, wherein the child is less than 36 months old.

3. The method of claim 1, wherein the child is at least 6 months old.

4. The method of claim 2, wherein the child is at least 6 months old but less than 36 months old.

5. The method of claim 1, wherein the immunogenic composition includes a subtype H3N2 influenza A strain antigen and the child receives one dose of vaccine.

6. The method of claim 1, wherein the immunogenic composition includes a subtype H1N1 influenza A strain antigen and the child receives more than one dose of vaccine.

7. The method of claim 1, wherein the child receives more than one dose of vaccine.

* * * * *

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic Construct
<221> NAME/KEY: misc_feature -continued

```
<222> LOCATION: 1, 3, 5, 7, 9, 11, 13, 15, 17, 19, 21, 23, 25
<223> OTHER INFORMATION: n = Inosine

<400> SEQUENCE: 1 ncncncnc ncncncnc ncncnc                              26

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct

<400> SEQUENCE: 2

Lys Leu Lys Leu Leu Leu Leu Leu Lys Leu Lys
1               5                   10
```